US012616834B2

(12) United States Patent
    Locke

(10) Patent No.: US 12,616,834 B2
(45) Date of Patent: May 5, 2026

(54) APPARATUSES, SYSTEMS, AND METHODS FOR THERAPY MODE CONTROL IN THERAPY DEVICES

(71) Applicant: KCI Manufacturing Unlimited Company, Athlone (IE)

(72) Inventor: Christopher Brian Locke, Bournemouth (GB)

(73) Assignee: KCI Manufacturing Unlimited Company, Westmeath (IE)

( * ) Notice: Subject to any disclaimer, the term of this patent is extended or adjusted under 35 U.S.C. 154(b) by 987 days.

(21) Appl. No.: 17/772,571

(22) PCT Filed: Nov. 6, 2020

(86) PCT No.: PCT/IB2020/060478
    § 371 (c)(1),
    (2) Date: Apr. 28, 2022

(87) PCT Pub. No.: WO2021/090267
    PCT Pub. Date: May 14, 2021

(65) Prior Publication Data
    US 2022/0395232 A1      Dec. 15, 2022

Related U.S. Application Data

(60) Provisional application No. 62/931,384, filed on Nov. 6, 2019.

(51) Int. Cl.
    *A61N 1/36*      (2006.01)
    *A61B 5/00*      (2006.01)
    *A61H 9/00*      (2006.01)

(52) U.S. Cl.
    CPC ......... *A61N 1/36031* (2017.08); *A61H 9/005* (2013.01); *A61B 5/0015* (2013.01);
    (Continued)

(58) Field of Classification Search
    CPC .......... A61F 13/05; A61M 1/90; A61H 9/005; A61H 9/0057; A61H 9/0085;
    (Continued)

(56) References Cited

U.S. PATENT DOCUMENTS

| | | | |
|---|---|---|---|
| 1,355,846 A | 10/1920 | Rannells | |
| 2,547,758 A | 4/1951 | Keeling | |
| | (Continued) | | |

FOREIGN PATENT DOCUMENTS

| | | | |
|---|---|---|---|
| AU | 550575 B2 | 3/1986 | |
| AU | 745271 B2 | 3/2002 | |
| | (Continued) | | |

OTHER PUBLICATIONS

International Search Report and Written Opinion Corresponding to Application No. PCT/IB2020/060478, mailed Mar. 31, 2021.
(Continued)

*Primary Examiner* — Paige Kathleen Bugg

(57)                ABSTRACT

This disclosure describes devices, systems, and methods related to therapy devices that are operable in multiple operating modes. An exemplary therapy device is configured to be coupled to a patient and includes a stimulation generator and a controller coupled to the stimulation generator. The controller is configured to transition the stimulation generator from operating in a first operating mode to operating in a second operating mode responsive to determining activity of the patient.

20 Claims, 9 Drawing Sheets

(52) U.S. Cl.
CPC .............. *A61B 5/445* (2013.01); *A61B 5/742* (2013.01); *A61H 2201/5071* (2013.01)

(58) Field of Classification Search
CPC .... A61H 2201/5071; A61H 2201/5079; A61H 2201/5082; A61H 2201/5084; A61H 2230/04–065; A61H 2230/25–255; A61N 1/32–322; A61N 1/18–28; A61B 5/445
USPC ........................................................ 601/15
See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,846,141 B2 | 12/2010 | Weston | |
| 8,062,273 B2 | 11/2011 | Weston | |
| 8,216,198 B2 | 7/2012 | Heagle et al. | |
| 8,251,979 B2 | 8/2012 | Malhi | |
| 8,257,327 B2 | 9/2012 | Blott et al. | |
| 8,398,614 B2 | 3/2013 | Blott et al. | |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |
| 8,679,081 B2 | 3/2014 | Heagle et al. | |
| 8,834,451 B2 | 9/2014 | Blott et al. | |
| 8,926,592 B2 | 1/2015 | Blott et al. | |
| 9,017,302 B2 | 4/2015 | Vitaris et al. | |
| 9,198,801 B2 | 12/2015 | Weston | |
| 9,211,365 B2 | 12/2015 | Weston | |
| 9,289,542 B2 | 3/2016 | Blott et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2012/0245483 A1* | 9/2012 | Lundqvist .............. A61B 5/296<br>600/546 | |
| 2013/0085551 A1* | 4/2013 | Bachinski .......... A61N 1/36034<br>607/59 | |
| 2014/0163491 A1 | 6/2014 | Schuessler et al. | |
| 2015/0080788 A1 | 3/2015 | Blott et al. | |
| 2017/0056650 A1* | 3/2017 | Cohen .................. A61N 1/3603 | |
| 2019/0240475 A1* | 8/2019 | Lawson ................... A61B 5/01 | |
| 2020/0061379 A1* | 2/2020 | Bogie .................... H05K 1/189 | |
| 2020/0268592 A1* | 8/2020 | Johnson ............... A61H 9/0057 | |
| 2020/0276367 A1* | 9/2020 | Seddon ................... A61M 1/96 | |
| 2022/0226559 A1* | 7/2022 | Locke .................... A61M 1/96 | |

FOREIGN PATENT DOCUMENTS

| | | | |
|---|---|---|---|
| AU | 755496 B2 | 12/2002 | |
| CA | 2005436 A1 | 6/1990 | |
| DE | 26 40 413 A1 | 3/1978 | |
| DE | 43 06 478 A1 | 9/1994 | |
| DE | 29 504 378 U1 | 9/1995 | |
| EP | 0100148 A1 | 2/1984 | |
| EP | 0117632 A2 | 9/1984 | |

(56)                    References Cited

FOREIGN PATENT DOCUMENTS

| EP | 0161865 A2 | 11/1985 | | |
|----|-----------|---------|---|---|
| EP | 0358302 A2 | 3/1990 | | |
| EP | 1018967 A1 | 7/2000 | | |
| GB | 692578 A | 6/1953 | | |
| GB | 2195255 A | 4/1988 | | |
| GB | 2 197 789 A | 6/1988 | | |
| GB | 2 220 357 A | 1/1990 | | |
| GB | 2 235 877 A | 3/1991 | | |
| GB | 2 329 127 A | 3/1999 | | |
| GB | 2 333 965 A | 8/1999 | | |
| JP | 4129536 B2 | 8/2008 | | |
| SG | 71559 | 4/2002 | | |
| WO | 80/02182 A1 | 10/1980 | | |
| WO | 87/04626 A1 | 8/1987 | | |
| WO | 90/010424 A1 | 9/1990 | | |
| WO | 93/009727 A1 | 5/1993 | | |
| WO | 94/20041 A1 | 9/1994 | | |
| WO | 96/05873 A1 | 2/1996 | | |
| WO | 97/18007 A1 | 5/1997 | | |
| WO | 99/13793 A1 | 3/1999 | | |
| WO | WO-2016103031 A1 * | 6/2016 | ............ | A61F 13/05 |
| WO | 2017087157 A1 | 5/2017 | | |
| WO | WO-2019072531 A1 * | 4/2019 | .......... | A61B 5/1032 |
| WO | 2020167547 A1 | 8/2020 | | |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ? uki?, Ž. Maksimovi?, ?. Radak, and . Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

(56) References Cited

OTHER PUBLICATIONS

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

* cited by examiner

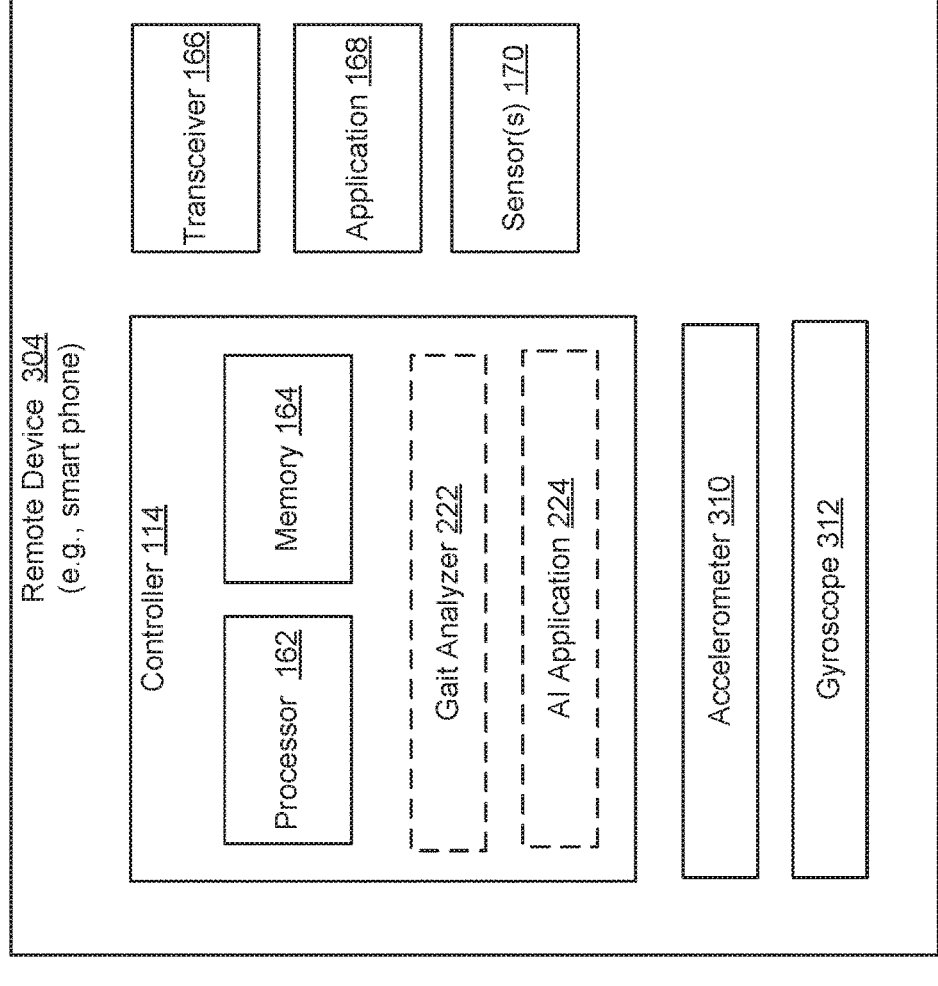
FIG. 3

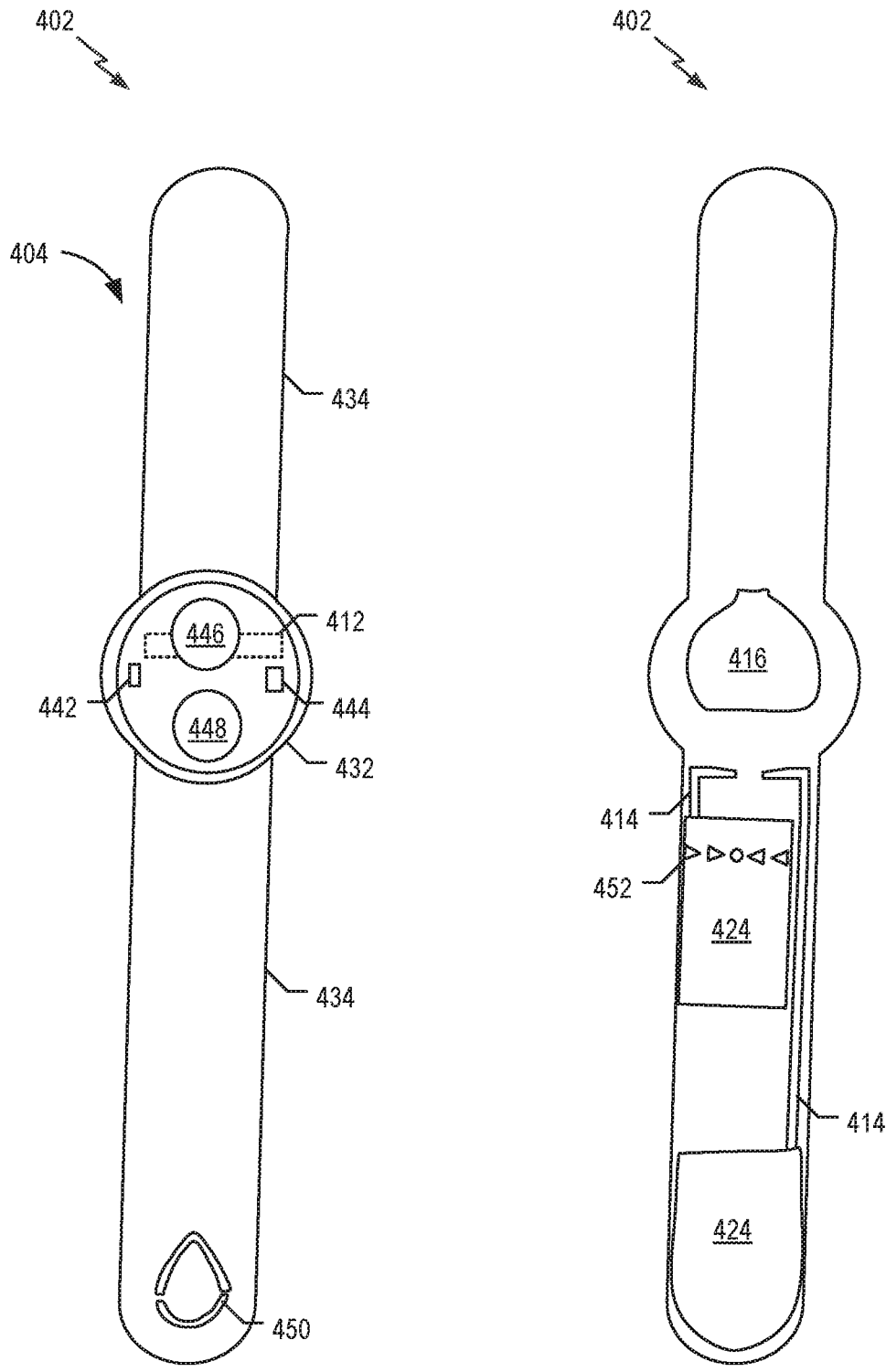
*FIG. 4A*          *FIG. 4B*

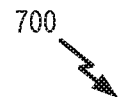
700
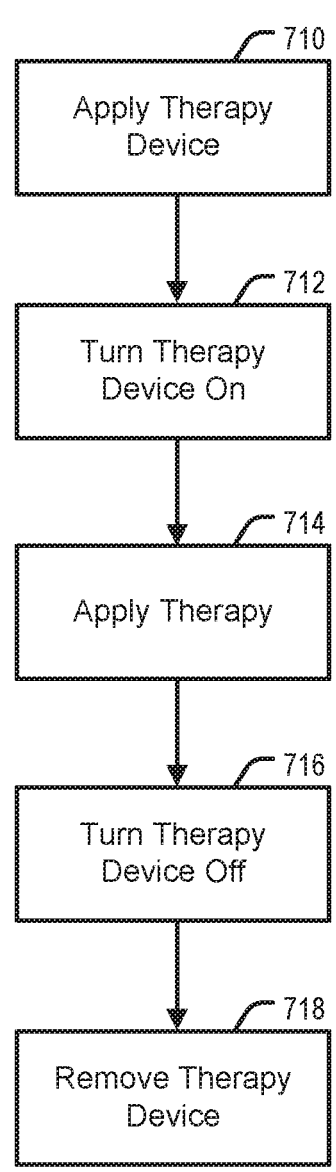
710
Apply Therapy
Device
712
Turn Therapy
Device On
714
Apply Therapy
716
Turn Therapy
Device Off
718
Remove Therapy
Device
*FIG. 7*

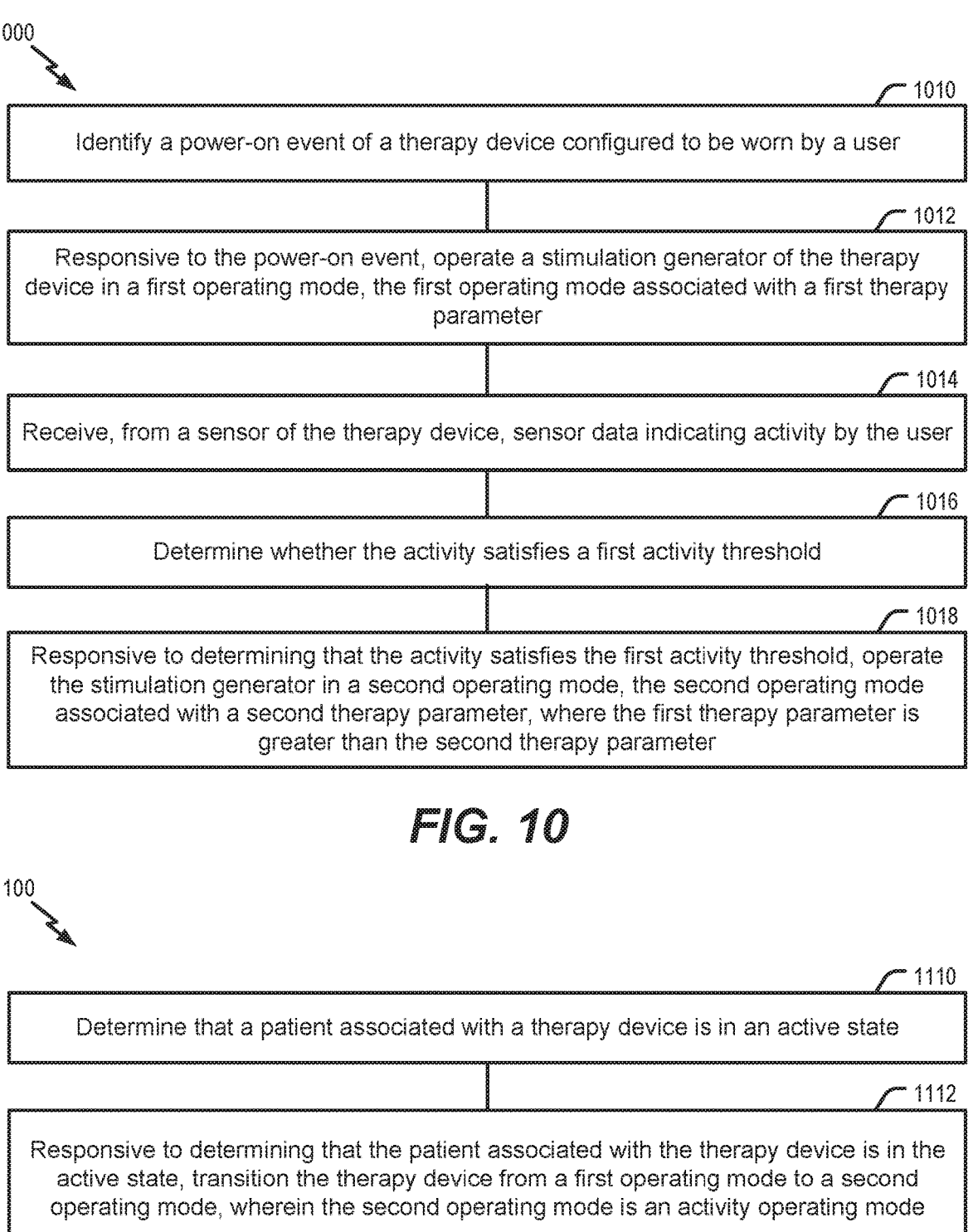

1000

1010

Identify a power-on event of a therapy device configured to be worn by a user

1012

Responsive to the power-on event, operate a stimulation generator of the therapy device in a first operating mode, the first operating mode associated with a first therapy parameter

1014

Receive, from a sensor of the therapy device, sensor data indicating activity by the user

1016

Determine whether the activity satisfies a first activity threshold

1018

Responsive to determining that the activity satisfies the first activity threshold, operate the stimulation generator in a second operating mode, the second operating mode associated with a second therapy parameter, where the first therapy parameter is greater than the second therapy parameter

Determine that a patient associated with a therapy device is in an active state

1112

Responsive to determining that the patient associated with the therapy device is in the active state, transition the therapy device from a first operating mode to a second operating mode, wherein the second operating mode is an activity operating mode

FIG. 11

APPARATUSES, SYSTEMS, AND METHODS FOR THERAPY MODE CONTROL IN THERAPY DEVICES

CROSS-REFERENCE TO RELATED APPLICATIONS

This application is a National Stage entry of PCT/IB2020/060478, filed Nov. 6, 2020, which claims the benefit of priority to U.S. Provisional Application No. 62/931,384, filed on Nov. 6, 2019, which is incorporated herein by reference in its entirety.

TECHNICAL FIELD

Aspects of the present disclosure relate generally to therapy devices, and more specifically, but not by way of limitation, to therapy devices that provide electric stimulation therapy or compression therapy.

BACKGROUND

Some types of therapy systems provide compression therapy to stimulate blood flow in veins and arteries to promote healing and recovery and/or alleviate particular conditions. Such compression therapy may be provided by electric or mechanical stimulation to a tissue site to stimulate blood flow and muscle activity.

With electric type stimulation therapy systems, an electrically conductive adhesive is generally used to adhere the therapy system (e.g., therapy device) to a patient. Such electrically conductive adhesives have relatively low bond/peel strengths as compared to other non-electrically conductive adhesives, and thus may be prone to shifting. Mechanical type stimulation therapy systems apply physical pressure, such as by direct contact (e.g., a massage head) or by a fluid (e.g., pressurized oxygen).

With both types of stimulation therapy systems, placement is important to facilitate proper and intended functioning of the therapy system. To illustrate, if the electrodes of an electric type stimulation therapy system are not in an intended or designed position relative to tissue intended to receive treatment, the treatment may be less effective and/or cause discomfort (e.g., pain) to the patient. As another illustration, similarly, if the physical force/pressure of the compression therapy is not in an intended or designed position relative to tissue intended to receive treatment, the treatment may be less effective and/or cause discomfort (e.g., pain) to the patient.

Conventional electrically conductive adhesives have a bond/peel strength that is designed to not cause damage to tissue during application or removal. Additionally, such conventional devices may be designed to be easily removed so that a patient can walk or workout without the device interfering or providing therapy or so that the patient can remove the therapy device when the patient desires a break or to sleep. However, because of such bond strength limitations and operational limitations, such electrically conductive adhesives may allow removal of the therapy device and repositioning or movement of the therapy device after application of the therapy device to a tissue site. Additionally, compression devices, such as compression sleeves, may be removed or repositioned by a user, such as when the patient is active. Thus, conventional stimulation therapy systems may not be repositioned properly or may become misaligned during use or from impact. Accordingly, the therapy devices may be reapplied incorrectly and may have reduced effectiveness and/or cause discomfort.

SUMMARY

This disclosure describes apparatus, systems, methods, and computer-readable storage devices for controlling therapy devices (e.g., a stimulation therapy device) in multiple operating modes, i.e., two or more operating modes. For example, a controller (e.g., a processor or other hardware) of a therapy device may be configured to operate a stimulation generator of the therapy device in one of multiple operating modes, such as a first operating mode (e.g., a "normal power operating mode"), a second operating mode (e.g., an "inactive or standby mode"), or a third operating mode (e.g., an activity or "reduced power operating mode"). Each of the different operating modes may provide respective benefits, and being able to operate the therapy device (e.g., stimulation generator thereof) in the different operating modes improves the flexibility of the therapy device, as compared conventional therapy devices or systems that are only configured to operate in a single operating mode. Such improved flexibility may enable the device to be designed to be non-removable throughout the day or in between servicing by a care provider. Therefore, such devices may alleviate the problems of misalignment that conventional patient removable therapy device have and may provide effective therapy in a wider range of conditions, such as when the user is active or when the user would like a break or reduced intensity therapy.

As an illustrative, non-limiting example, an activity or reduced power operating mode may provide reduced intensity therapy or temporarily cease therapy when a user is active, such as walking, working out, etc. To illustrate, the muscles of the tissue site may be in use for the activity, and thus stimulation or compression induced by the therapy device to the muscles may not be as effective and/or may cause discomfort or the activity to be impaired. By entering into an active mode, such as by user input or automatically based on sensor data, the therapy device may account for activity of a patient and provide more effective therapy (including no therapy) when the user is active and may not need to be removed. Also such a system may encourage a user to be active, that is, the user may stop or reduce therapy by being active. As natural activity is often the most effective treatment, such a system may further enhance recovery.

Additionally, the use of two or more of the multiple operating modes may enable user convenience and/or power savings. To illustrate, such therapy devices may enable the use of a reduced power mode which may be more comfortable for the user in certain conditions, such as when active, sleeping, in public, desiring a break, etc., and which may provide the additional benefit of power savings.

Additionally, the therapy systems described herein may include multiple sensors and analyzers to determine activity, infection, misplacement of the device, removal of the device, non-compliance with a treatment plan, or a combination thereof. For example, the system may use differential temperature sensors to determine an infection at the tissue site. As another example, the system may determine a walking speed or activity level based on a gait analyzer and artificial intelligence applications or artificial intelligence generated models or thresholds. As yet another example, activity or a condition may be determined based on sensor data from multiple different types of sensors. To illustrate, one or more of skin hydration, temperature, heart rate, or inertial sensors may be used to determine activity. In some implementations, the therapy device is controllable by a remote device and may send notifications, sensor data, and/or log data to one or more remote devices. Thus, a patient and/or care provider may control and adjust the therapy device remotely over a wireless connection, such as over Bluetooth or WI-FI.

Thus, the present disclosure describes a therapy device configured to operate in multiple operating modes. The multiple operating modes may include a normal power operating mode and one or more activity modes, which may have increased effectiveness and comfort when a user is active. Therefore, the therapy devices described herein provides for increased levels of comfort and control of stimulation therapy and enable conditional or condition based stimulation therapy. Accordingly, the systems described herein may enable improved care and therapy, thereby advancing patient comfort and confidence in the treatment.

In some embodiments of the present devices (e.g., control device), the present devices comprise: a processor configured to control a therapy device; and a memory coupled to the processor and configured to store instructions. The processor is configured to execute the instructions stored at the memory to: determine that a patient associated with the therapy device is in an active state; and transition the therapy device from a first operating mode to a second operating mode, wherein the second operating mode is an activity operating mode.

In some of the foregoing embodiments of the present devices, the activity operating mode comprises a reduced intensity stimulation operating mode as compared to the first operating mode. Additionally or alternatively, the in the activity operating mode comprises an inactive or standby operating mode.

In some of the foregoing embodiments of the present devices, the therapy device includes a stimulation generator configured to provide electric stimulation therapy. Additionally or alternatively, the therapy device includes a pump configured to provide compression therapy.

In some of the foregoing embodiments of the present devices, the processor is further configured to transition the therapy device to a third operating mode, wherein the third operating mode is a second activity operating mode, a night time mode, or a user initiated break mode. Additionally, or alternatively, the present devices further comprise one or more sensors coupled to the processor, the one or more sensors configured to generate sensor data indicating an activity level of the patient.

In some of the foregoing embodiments of the present devices, the one or more sensors comprise an inertial sensor, a heart rate sensor, temperature sensor, or a combination thereof. Additionally, or alternatively, the present devices further comprise a timer, a moisture sensor, an electrical sensor, or a combination thereof.

In some of the foregoing embodiments of the present devices, the present devices further comprise a pressure sensor coupled to a dressing configured to be coupled to a tissue site of the patient, the pressure sensor configured to measure a compression pressure at the dressing and to send pressure data to the controller, the pressure data indicative of the compression pressure.

In some embodiments of the present devices (e.g., a therapy device), the present devices comprise: a stimulation generator configured to provide stimulation therapy to a tissue site of a patient; and a controller coupled to the stimulation generator and configured to transition the stimulation generator from operating in a first operating mode to operating in a second operating mode responsive to determining that the patient is in an active state.

In some of the foregoing embodiments of the present devices, the second operating mode includes a second therapy parameter less than a first therapy parameter of the first operating mode, wherein the therapy parameter includes, voltage, drive voltage, current, duty cycle, compression pressure, or a combination thereof. Additionally, or alternatively, the stimulation generator comprises a pump, and further comprising a pressure sensor coupled to the pump and configured to measure a pressure output by the pump and to send pressure data to the controller, the pressure data indicative of the pressure output.

In some of the foregoing embodiments of the present devices, the present devices further comprise a pressure sensor coupled to a dressing configured to be coupled to a wound site, the pressure sensor configured to measure the pressure at the dressing and to send pressure data to the controller, the pressure data indicative of the pressure. Additionally or alternatively, the present devices further comprise a timer, the timer configured to measure a duration of therapy applied to the patient and generate timer data, wherein the controller is further configured to determine one or more durations of therapy modes applied to the patient based on the timer data.

In some of the foregoing embodiments of the present devices, the present devices further comprise a temperature sensor, the temperature sensor configured to measure a temperature of the tissue site of the patient and generate temperature data, wherein the controller is further configured to determine the temperature of the patient based on the temperature data. Additionally, or alternatively, the temperature sensor comprises a thermocouple coupled to an adhesive of the therapy device, and wherein the controller is further configured to determine an infection, a perfusion level, or both based on the temperature data.

In some of the foregoing embodiments of the present devices, the present devices further comprise a pressure sensor, the pressure sensor configured to measure a compression pressure applied to the patient and generate pressure data, wherein the controller is further configured to determine the compression pressure applied to the patient based on the pressure data.

In some of the foregoing embodiments of the present devices, the present devices further comprise a heart rate sensor, the heart rate sensor configured to measure a heart rate of the patient and generate heart rate data, wherein the controller is further configured to determine a heart rate of the patient based on the heart rate data. In some such implementations, the heart rate sensor comprises an optical pulse sensor, and wherein the controller is further configured to determine an infection, a perfusion level, or both based on the heart rate data.

In some of the foregoing embodiments of the present devices, the present devices further comprise an inertial sensor coupled to the therapy device, the inertial sensor configured to measure an inertia of the therapy device and generate inertia data, wherein the controller is further configured to determine an inertia of the patient based on the inertia data. In some such implementations, the inertial sensor comprises an accelerometer, a gyroscope, or both.

In some of the foregoing embodiments of the present devices, the controller is further configured to select a reduced power mode or an inactive mode based on comparing the inertia of the patient to one or more inertial thresholds. Additionally, or alternatively, the controller further includes a gait analyzer configured to determine a gait based on the inertia data.

In some of the foregoing embodiments of the present devices, the present devices further comprise a moisture sensor coupled to the therapy device, the moisture sensor configured to measure a hydration of tissue of the tissue site, humidity of the tissue site, or both, and generate moisture data, wherein the controller is further configured to determine an infection based on the moisture data. In some such implementations, the moisture sensor comprises a skin hydration sensor, and wherein the controller is further configured to determine an infection, a perfusion level, or both based on the moisture data.

In some of the foregoing embodiments of the present devices, the present devices further comprise an electrical sensor coupled to the therapy device, the electrical sensor configured to measure an electrical parameter of the stimulation generator and generate electrical data, wherein the electrical parameter include voltage, current, or both. In some such implementations, the electrical sensor comprises a current draw sensor, and wherein the controller is further configured to determine if the therapy device is misplaced, if the therapy device has been removed, or both, based on the electrical data.

In some of the foregoing embodiments of the present devices, the present devices further comprise a pH sensor coupled to the therapy device, the pH sensor configured to measure a pH of tissue of the tissue site and generate pH data. Additionally, or alternatively, the controller is further configured to determine a condition of the tissue based on the pH data. In some of the foregoing embodiments of the present devices, the controller further includes an artificial intelligence (AI) application configured to determine activity, select an operating mode, adjust a threshold, or a combination thereof, based on AI models and sensor data. Additionally, or alternatively, the controller is further configured to output a notification via the therapy device, a notification to a remote device of the patient, a notification to a remote device associated with a care provider, or a combination thereof, responsive to determining that a therapy condition is has not been satisfied.

In some of the foregoing embodiments of the present devices, the controller is further configured to generate a log of operating modes, operating mode durations, conditions satisfied, conditions failed, sensor data, or a combination thereof. In some such implementations, the controller is configured to send log data to a mobile device associated with a patient care of the patient.

In some embodiments of the present systems (e.g., a therapy system), the therapy system comprises: a therapy device configured to provide therapy to a patient; and a control device coupled to the therapy device and configured to transition the therapy device from operating in a first operating mode to operating in a second operating mode responsive to determining that the patient is in an active state.

In some of the foregoing embodiments of the present systems, the control device comprises a remote device separate from the therapy device and communicatively coupled to the therapy device, wherein the remote device is configured to adjust settings of the therapy device, receive notifications from the therapy device, or both.

Additionally, or alternatively, wherein the therapy device includes or corresponds to an electric stimulation therapy device and the control device is integrated with the therapy device, and wherein the therapy device is configured to be coupled to a tissue site of the patient.

In some of the foregoing embodiments of the present systems, the present systems further comprise a dressing coupled to the therapy device and configured to couple to a tissue site of a patient.

In some such implementations, the dressing comprises an electric stimulation dressing. In some of the foregoing embodiments of the present systems, the dressing comprises a compression dressing.

In some embodiments of the present methods (e.g., a method for providing therapy), the present methods comprise: identifying a power-on event of a therapy device, the therapy device configured to be worn by a user; responsive to the power-on event, operating a stimulation generator of the therapy device in a first operating mode, the first operating mode associated with a first therapy parameter; receiving, from a sensor of the therapy device, sensor data indicating activity by the user; determining whether the activity satisfies a first activity threshold; and responsive to determining that the activity satisfies the first activity threshold, operating the stimulation generator in a second operating mode, the second operating mode associated with a second therapy parameter, wherein the first therapy parameter is greater than the second therapy parameter.

In some of the foregoing embodiments of the present methods, operating the stimulation generator in the first operating mode comprises sending one or more control signals indicating the first operating mode to the stimulation generator. Additionally, or alternatively, the second therapy parameter comprises a voltage, a drive voltage, a current, a duty cycle, a compression pressure, or a combination thereof.

In some of the foregoing embodiments of the present methods, the stimulation generator comprises a pump, and the present methods further comprise: receiving, from a pressure sensor, pressure data indicating a pressure applied by the pump; comparing the pressure to a pressure threshold; and responsive to determining that the pressure is greater than the pressure threshold, reducing a duty cycle of the pump.

In some of the foregoing embodiments of the present methods, the present methods further comprise: receiving, from the sensor of the therapy device, second sensor data indicating second activity by the user; comparing the second sensor data to a second activity threshold; and responsive to determining that the second activity is greater than the second activity threshold, operating the stimulation generator in a third operating mode, the third operating mode associated with a third therapy parameter, wherein the third therapy parameter is less than the second therapy parameter. Additionally, or alternatively, the present methods further comprise: receiving, from a remote device, second sensor data indicating second activity by the user; comparing the second sensor data to a second activity threshold; and responsive to determining that the second activity is greater than the second activity threshold, operating the stimulation generator in a third operating mode, the third operating mode associated with a third therapy parameter, wherein the third therapy parameter is less than the second therapy parameter. In some such implementations, the third operating mode comprises a second activity mode and corresponds to an inactive or sleep mode.

In some of the foregoing embodiments of the present methods, the present methods further comprise: receiving first temperature data from a first temperature sensor coupled to the tissue site; receiving second temperature data from a second temperature sensor coupled to a second tissue site; determining a temperature difference based on the first temperature data and the second temperature data; comparing the temperature difference to a temperature threshold; and determining whether the tissue site has an infection based on comparing the temperature difference to a temperature threshold.

In some embodiments of the present computer-readable storage devices, the present computer readable storage device store instructions that, when executed by a processor, cause the processor to perform operations to provide wound therapy. In some such embodiments, the operations comprise: identifying a power-on event of a therapy device, the therapy device configured to be worn by a user; responsive to the power-on event, operating a stimulation generator of the therapy device in a first operating mode, the first operating mode associated with a first therapy parameter; receiving, from a sensor of the therapy device, sensor data indicating activity by the user; determining whether the activity satisfies a first activity threshold; and responsive to determining that the activity satisfies the first activity threshold, operating the stimulation generator in a second operating mode, the second operating mode associated with a second therapy parameter, wherein the first therapy parameter is greater than the second therapy parameter.

In some of the foregoing embodiments of the present computer-readable storage devices, the processor is further configured to perform the operations of adjusting the first activity threshold based on care provider input received from a remote device. Additionally, or alternatively, the processor is further configured to perform the operations of adjusting the first activity threshold based on a control signal from an artificial intelligence application.

In some of the foregoing embodiments of the present computer-readable storage devices, the processor is further configured to perform the operations of: receiving a user input indicating a request to enter a break operating mode; determining a count value of break operating modes; comparing the count value to a break operating mode threshold; and determining whether to enter the break operating mode based on comparing the count value to the break operating mode threshold. Additionally, or alternatively, the processor is further configured to perform the operations of: receiving a user input indicating a request to enter a reduced intensity operating mode; determining a duration of time spent in the reduced intensity operating mode; comparing the duration to a reduced intensity operating mode threshold; and determining whether to enter the reduced intensity operating mode based on comparing the duration to the reduced intensity operating mode threshold.

In some of the foregoing embodiments of the present computer-readable storage devices, the processor is further configured to perform the operations of: receiving a skin hydration data from a moisture sensor; receiving current draw data from a current sensor; and determining whether the device is incorrectly positioned or has been removed based on the skin hydration data, the current draw data, and one or more thresholds. Additionally, or alternatively, the processor is further configured to perform the operations of: receiving, from a pulse rate sensor of the therapy device, pulse rate data indicating a pulse rate of the user; determining a pulse rate threshold based on the activity indicated by the activity data; and determining whether the pulse rate data satisfies the pulse rate threshold, wherein operating the stimulation generator in the second operating mode is further responsive to determining whether the pulse rate data satisfies the pulse rate threshold.

In some embodiments of the present therapy devices, the present therapy devices comprise: stimulation means for providing stimulation therapy to a tissue site of a patient; and control means coupled to the stimulation means and configured to transition the stimulation means between multiple operating modes, wherein the multiple operating modes include a normal mode and an activity mode.

In some of the foregoing embodiments of therapy devices, wherein the multiple operating modes further includes one or more of a second activity mode, a night time mode, a reduced intensity mode, or a break mode.

As used herein, various terminology is for the purpose of describing particular implementations only and is not intended to be limiting of implementations. For example, as used herein, an ordinal term (e.g., "first," "second," "third," etc.) used to modify an element, such as a structure, a component, an operation, etc., does not by itself indicate any priority or order of the element with respect to another element, but rather merely distinguishes the element from another element having a same name (but for use of the ordinal term). The term "coupled" is defined as connected, although not necessarily directly, and not necessarily mechanically. Additionally, two items that are "coupled" may be unitary with each other. To illustrate, components may be coupled by virtue of physical proximity, being integral to a single structure, or being formed from the same piece of material. Coupling may also include mechanical, thermal, electrical, communicational (e.g., wired or wireless), or chemical coupling (such as a chemical bond) in some contexts.

The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. As used herein, the term "approximately" may be substituted with "within 10 percent of" what is specified. Additionally, the term "substantially" may be substituted with "within [a percentage] of" what is specified, where the percentage includes. 1, 1, or 5 percent; or may be understood to mean with a design, manufacture, or measurement tolerance. The phrase "and/or" means and or. To illustrate, A, B, and/or C includes: A alone, B alone, C alone, a combination of A and B, a combination of A and C, a combination of B and C, or a combination of A, B, and C. In other words, "and/or" operates as an inclusive or. Similarly, the phrase "A, B, C, or a combination thereof" or "A, B, C, or any combination thereof" includes: A alone, B alone, C alone, a combination of A and B, a combination of A and C, a combination of B and C, or a combination of A, B, and C.

The terms "comprise" (and any form of comprise, such as "comprises" and "comprising"), "have" (and any form of have, such as "has" and "having"), and "include" (and any form of include, such as "includes" and "including"). As a result, an apparatus that "comprises," "has," or "includes" one or more elements possesses those one or more elements, but is not limited to possessing only those one or more elements. Likewise, a method that "comprises," "has," or "includes" one or more steps possesses those one or more steps, but is not limited to possessing only those one or more steps.

Any aspect of any of the systems, methods, and article of manufacture can consist of or consist essentially of-rather than comprise/have/include-any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb. Additionally, it will be understood that the term "wherein" may be used interchangeably with "where."

Further, a device or system that is configured in a certain way is configured in at least that way, but it can also be configured in other ways than those specifically described. The feature or features of one embodiment may be applied to other embodiments, even though not described or illustrated, unless expressly prohibited by this disclosure or the nature of the embodiments.

Some details associated with the aspects of the present disclosure are described above, and others are described below. Other implementations, advantages, and features of the present disclosure will become apparent after review of the entire application, including the following sections: Brief Description of the Drawings, Detailed Description, and the Claims.

BRIEF DESCRIPTION OF THE DRAWINGS

A further understanding of the nature and advantages of the present disclosure may be realized by reference to the following drawings. The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

FIG. 3 is a block diagram of an example of a remote device of a therapy system;

FIG. 4 is a block diagram of an example of a therapy device for electric stimulation therapy;

FIG. 7 is a flowchart illustrating an example of a method of using a therapy device;

FIG. 10 is a flowchart illustrating an example of a method of operating a stimulation generator of a therapy device; and FIG. 11 is a flowchart illustrating an example of another method of operating a stimulation generator of a therapy device.

DETAILED DESCRIPTION

Figure 1:
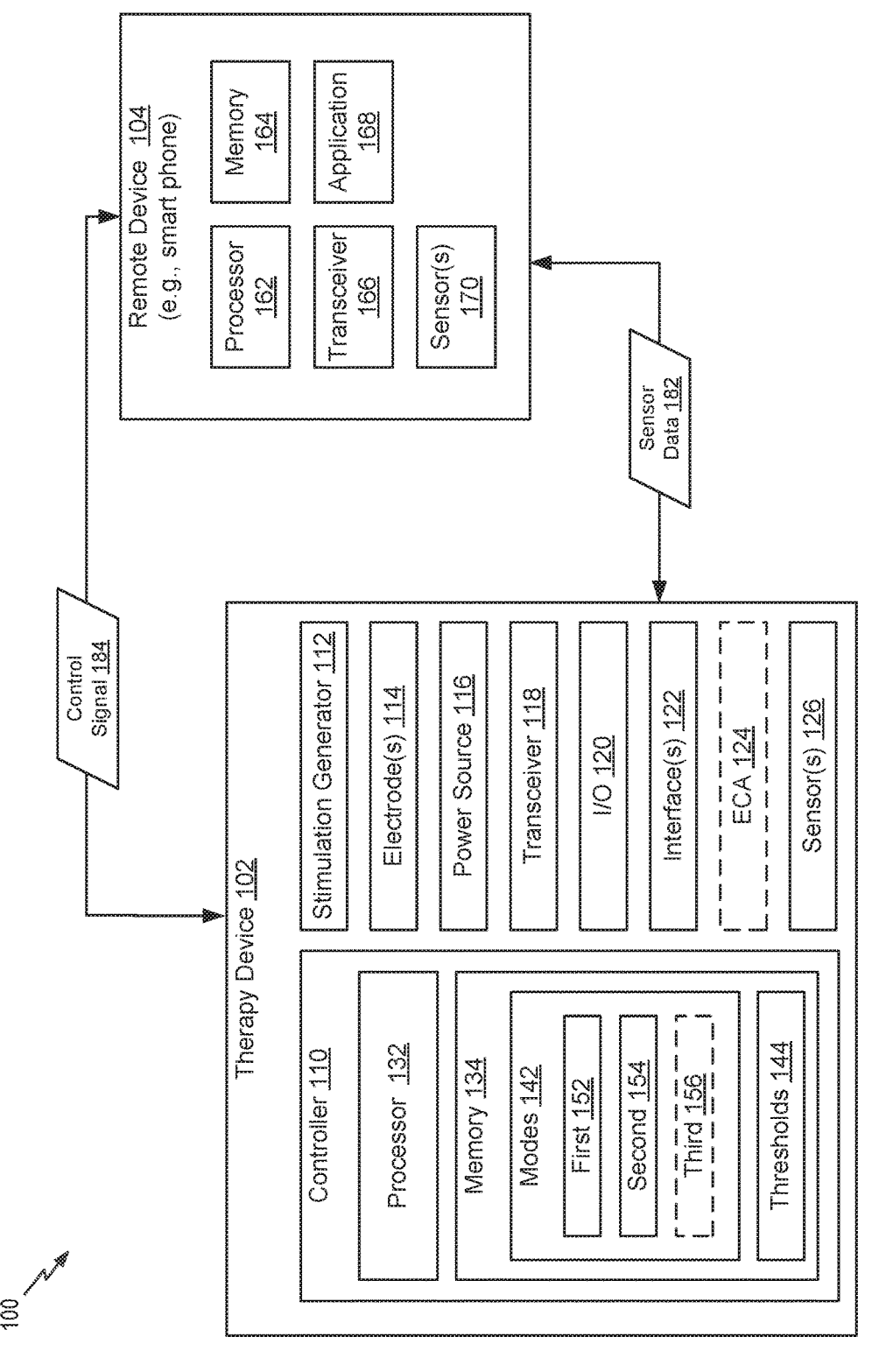
FIG. 1 is a block diagram of an example of a therapy system for stimulation therapy.

As used herein, the terms "tissue site" and "target tissue" as used herein can broadly refer to a wound (e.g., open or closed), a tissue disorder, and/or the like located on or within tissue, such as, for example, bone tissue, adipose tissue, muscle tissue, neural tissue, dermal tissue, vascular tissue, connective tissue, cartilage, tendons, ligaments, and/or the like. The terms "tissue site" and "target tissue" as used herein can also refer to a surrounding tissue area(s) and/or areas of tissue that are not necessarily wounded or exhibit a disorder, but include tissue that would benefit from tissue generation and/or tissue that may be harvested and transplanted to another tissue location. The terms "tissue site" and "target tissue" may also include incisions, such as a surgical incision. In some implementations, "target tissue" may correspond or refer to a wound, and "tissue site" may correspond or refer to a tissue area(s) surrounding and including the target tissue. Additionally, the term "wound" as used herein can refer to a chronic, subacute, acute, traumatic, and/or dehisced incision, laceration, puncture, avulsion, and/or the like, a partial-thickness and/or full thickness burn, an ulcer (e.g., diabetic, pressure, venous, and/or the like), flap, and/or graft. A wound may include chronic, acute, traumatic, subacute, and dehisced wounds, partial-thickness burns, ulcers (such as diabetic, pressure, or venous insufficiency ulcers), flaps, grafts, and fistulas, for example.

The term "positive-pressure" (or "hyperbaric") as used herein generally refers to a pressure greater than a local ambient pressure, such as the ambient pressure in a local environment external to a sealed therapeutic environment (e.g., an internal volume). In most cases, this positive-pressure will be greater than the atmospheric pressure at which the patient is located. Alternatively, the positive-pressure may be greater than a hydrostatic pressure associated with tissue at the tissue site. Unless otherwise indicated, values of pressure stated herein are gauge pressures. References to increases in positive-pressure typically refer to an increase in absolute pressure, and decreases in positive-pressure typically refer to a decrease in absolute pressure. Additionally, the process of increasing pressure may be described illustratively herein as "applying", "delivering," "distributing," "generating", or "providing" positive-pressure, for example.

The term "reduced-pressure" (and "negative-pressure" or "hypobaric") as used herein generally refers to a pressure less than a local ambient pressure, such as the ambient pressure in a local environment external to a sealed therapeutic environment (e.g., an internal volume). In most cases, this reduced-pressure will be less than the atmospheric pressure at which the patient is located. Alternatively, the reduced-pressure may be less than a hydrostatic pressure associated with tissue at the tissue site. Unless otherwise indicated, values of pressure stated herein are gauge pressures. References to increases in reduced-pressure typically refer to a decrease in absolute pressure, and decreases in reduced-pressure typically refer to an increase in absolute pressure. Additionally, the process of reducing pressure may be described illustratively herein as "applying", "delivering," "distributing," "generating", or "providing" reduced-pressure, for example.

The term "fluid" may refer to liquid, gas, air, or a combination thereof. The term "fluid seal," or "seal," means a seal adequate to maintain a pressure differential (e.g., positive-pressure or reduced-pressure) at a desired site given the particular pressure source or subsystem involved. Similarly, it may be convenient to describe certain features in terms of fluid "inlet" or "outlet" in such a frame of reference. However, the fluid path may also be reversed in some applications, such as by substituting a reduced-pressure source (negative or hypobaric pressure source) for a positive-pressure source, and this descriptive convention should not be construed as a limiting convention.

FIG. 1 illustrates block diagram of an example of an illustrative therapy system 100 including a controller configured to operate a therapy device in multiple operating. System 100 includes a therapy device 102 and a remote device 104 and is configured to provide therapy to a tissue site of patient. As illustrated in the example of FIG. 1, the therapy device 102 is a stimulation therapy device, such as an electric stimulation device.

The therapy device 102 is coupled to the tissue site of the patient by the electrically conductive adhesive (ECA) 124. Therapy device 102 may be controlled by remote device 104, as illustrated in the example of FIG. 1. In other examples, the therapy device 102 is controlled internally, i.e. by a control device that is integrated into therapy device 102.

As illustrated by the example of FIG. 1, therapy device 102 includes a controller 110, a stimulation generator 112, one or more electrodes 114, a power source 116, a transceiver 118, input/output (I/O) devices 120, one or more interfaces 122, and one or more sensors 126. Therapy device 102 is configured to receive or includes ECA 124, as described further herein.

Controller 110 includes a processor 132 and a memory 134. Controller 110 may be configured to control operations of therapy device 102. Memory 134, such as a non-transitory computer-readable storage medium, may include volatile memory devices (e.g., random access memory (RAM) devices), nonvolatile memory devices (e.g., read-only memory (ROM) devices, nanotube ribbon crossbar memory (NTRCM) devices, programmable read-only memory, and flash memory), or both. Memory 134 may be configured to store instructions, one or more thresholds, and one or more data sets. Instructions (e.g., control logic) may be configured to, when executed by the processor 132, cause the processor 132 to perform operations as described further here. For example, the processor 132 may perform operations as described with reference to FIGS. 1-4, 5A, and 6-11. The one or more thresholds and one or more data sets may be configured to cause the processor 132 to generate control signals. For example, the processor 132 may generate and send control signals responsive to receiving sensor data from one or more of therapy device 102 or remote device 104, such as exemplary sensor data 182 from remote device 104.

In some implementations, processor 132 may include or correspond to a microcontroller/microprocessor, a central processing unit (CPU), a field-programmable gate array (FPGA) device, an application-specific integrated circuits (ASIC), another hardware device, a firmware device, or any combination thereof. Processor 132 may be configured to execute instructions to initiate or perform one or more operations described with reference to FIG. 1 and/or one or more of the other figures described herein.

Stimulation generator 112 is configured to provide stimulation therapy. Stimulation therapy may be provided with alternating current (AC) waveforms, direct current (DC) waveforms, and/or pulsed current waveforms, or a combination thereof. Therapy device 102 may optionally include a converter or inverter. The converter or inverter may be coupled to the pulse or stimulation generator 112. Converters and inverters may include or correspond to electrical devices which convert voltages between AC and DC, such as a converter converts the voltage from AC to DC and an inverter converts the voltage from DC to AC. Stimulation generator 112 may be configured to generate pulses of therapy based on signals from controller 110 (e.g., processor 132 thereof).

Stimulation generator 112 may additionally be coupled to electrodes 114. One or more electrodes 114 are configured to provide stimulation therapy to tissue site. Direct current therapy may maintain one electrode of electrodes 114 as the anode and another electrodes of electrodes 114 as the cathode. For alternating current, electrodes 114 may alternate their polarity each cycle. As an illustrative example of electrodes, one or more electrodes 114 may be metal (e.g., copper, granite, silver, titanium, brass, platinum), wires, conductive trace, or other conductive material.

Although illustrated as an electric stimulation device in FIG. 1, stimulation generator 112 may include or correspond to a mechanical stimulation generator in other implementations. For example, stimulation generator 112 may include massaging members which provide therapeutic massage to a tissue site. As another example, stimulation generator 112, such as pump, may provide pressure stimulation with a fluid, such as air or oxygen.

Power source 116 is configured to provide power to therapy device, such as controller 110 and/or stimulation generator 112 thereof. As an illustrative non-limiting example, power source 116 is a battery. In some implementations, power source 116 is removable from therapy device 102. Additionally or alternatively, power source 116 is rechargeable, such as a rechargeable battery.

In some implementations, therapy device 102 can include or can be configured to communicate with one or more I/O devices 120. I/O device 120 may include a mouse, a keyboard, a display device, the camera, other I/O devices, or a combination thereof. In some implementations, the processor 132 generates and sends control signals responsive to receiving one or more user inputs via the one or more I/O devices 120.

The one or more interfaces 122 may include a network interface and/or a device interface configured to be communicatively coupled to one or more other devices, such as controller 110, stimulation generator 112, and/or the remote device 104. For example, the one or more interfaces 122 may include a transmitter, a receiver, or a combination thereof (e.g., a transceiver 118), and may enable wired communication, wireless communication, or a combination thereof.

Therapy device 102 is configured to receive or includes the ECA 124. The ECA 124 may include a pressure sensitive adhesive that is configured to receive electricity from the electrodes 114 and transport the electricity to the tissue site. As an illustrative, non-limiting example, the ECA 124 include or corresponds to a hydrocolloid adhesive. In other implementations, the ECA 124 includes and electrically conductive switchable adhesive (ECSA) (e.g., a conductive light switchable adhesive, a non-conductive switchable adhesive with a conductive trace, or a non-conductive switchable adhesive with a conductive adhesive as a few non-limiting examples).

The one or more sensors 126 are configured to generate sensor data 182. The one or more sensors 126 may include multiple different types of sensors, and examples thereof are described further with reference to FIG. 2. The sensor data 182 may be sent to the controller 110 and/or the remote device 104 for processing. In some implementations, the sensor data 182 is processed at the therapy device 102 and a notification or control signal 184 is transmitted to the remote device 104. The notification may indicate or identify an action or status of the therapy device 102, such as misalignment of the therapy device or a status of the power source 116 of the therapy device 102.

Remote device 104, when included, may be configured to control therapy device 102. An illustrative example is represented in FIG. 1, such as when the therapy system 100 includes remote device 104, remote device 104 include a processor 162 and a memory 164. Processor 162 can be configured to perform operations related to controlling or communicating with the therapy device 102. One or more thresholds 144 and one or more data sets may be configured to cause the processor 162 to generate control signals, such as control signal 184, and send the control signals to the therapy device 102. Stimulation modes may be switched or adjusted based on comparing sensor data 182 to one or more thresholds, one or more data sets, or a combination thereof. For example, for switching between modes 142, a particular mode (e.g., a second mode 154) may be selected and used instead of a current mode (e.g., first mode 152) based on comparing sensor data 182 to one or more thresholds 144, one or more data sets, or a combination thereof.

As another example, for adjusting a particular mode, one or more the mode parameters may be changed adjusted based on comparing sensor data 182 to one or more thresholds 144, one or more data sets, or a combination thereof. To illustrate, one or more of the following therapy parameters may be adjusted, a type of therapy, an intensity of therapy, a frequency of therapy, a duty cycle of therapy, etc.

In some implementations, processor 162 may include or correspond to a microcontroller/microprocessor, a central processing unit (CPU), a field-programmable gate array (FPGA) device, an application-specific integrated circuits (ASIC), another hardware device, a firmware device, or any combination thereof. Processor 162 may be configured to execute instructions to initiate or perform one or more operations described further herein.

Memory 164, such as a non-transitory computer-readable storage medium, may include volatile memory devices (e.g., random access memory (RAM) devices), nonvolatile memory devices (e.g., read-only memory (ROM) devices, nanotube ribbon crossbar memory (NTRCM) devices, programmable read-only memory, and flash memory), or both. Memory 164 may be configured to store instructions, one or more thresholds 144, and one or more data sets. Instructions (e.g., control logic) may be configured to, when executed by the processor 162, cause the processor 162 to perform operations as described further here. Memory 164 may further be configured to communicate with or include application 168. Application 168 may include instructions, a program or group of programs, or a program configured for a mobile phone.

Remote device 104 may include or correspond to an electronic device such as a communications device, a mobile phone, a cellular phone, a satellite phone, a computer, a tablet, a portable computer, a display device, a media player, or a desktop computer. Additionally, or alternatively, the remote device 104 may include a personal digital assistant (PDA), a monitor, a computer monitor, a television, any other device that includes a processor or that stores or retrieves data or computer instructions, or a combination thereof. Remote device 104 may further include a transceiver 166 configured to transmit and receive data. As illustrated in FIG. 1, transceivers 118 and 166 can be configured to transmit and/or receive sensor data 182 and/or control signals 184.

Prior to operation, therapy device 102 is attached to a patient. During operation, therapy device 102 provides therapy to the patient. Therapy device 102 provides electrical signals to the patient via electrodes 114 and ECA 124. Therapy device 102 may start, adjust, and/or stop the therapy (e.g., the electrical signals) based on sensor data 182, inputs (e.g., control signal 184), or a combination thereof. The sensor data 182 may be generated by therapy device 102 and/or remote device 104. The control signals 184 may be generated by therapy device 102 and/or remote device 104. Thus, as an illustrative, non-limiting example, remote device 104 receives sensor data 182 from therapy device 102, generates control signal 184, sends the control signal 184 to therapy device 1025 to adjust therapy.

Adjusting therapy may include selecting a particular mode (e.g., 152-156) of modes 142 or adjusting parameters of one or more modes (e.g., 152-156) of modes 142. For example, a nighttime mode may be selected based on time. As another example, an active or activity mode may be selected based on heart rate, inertia data, etc. or a combination thereof. As yet another example, an inactive or break mode and/or a reduced intensity mode may be selected based on user input and/or one or more conditions, such as time or number conditions for implementation such modes. Accordingly, a user can implement a break in treatment or a reduced level of treatment for a period of time. Additional details of mode switching is described with reference with FIGS. 2, 3, and 7-11.

As an example adjusting parameters of one or more modes, a time/duration or number of times a particular mode may be selected may be adjusted by a user or a care provider. To illustrate, a doctor may remotely change a threshold used in determining whether the device can enter into a break mode using remote device 104. As another example of adjusting parameters of one or more modes, an intensity of a particular mode may be adjusted based on patient care provide input and/or sensor data. To illustrate, a doctor may remotely change a frequency or voltage used in a particular mode using remote device 104. As another illustration, a user may adjust a heart rate parameter or cause a heart rate parameter to be adjusted (e.g., enter in an age) using therapy device 102 (e.g., I/O 120 thereof) or remote device (e.g., application 168 thereof). Additional details of mode switching is described with reference with FIGS. 2, 3, and 7-11. After operation, therapy device 102 is detached from the patient.

Thus, system 100 enables a therapy device 102 which provides for increased levels of control of stimulation therapy and for conditional stimulation therapy. Accordingly, the systems described herein may enable improved care and therapy, thereby advancing patient comfort and confidence in the treatment.

Figure 2:
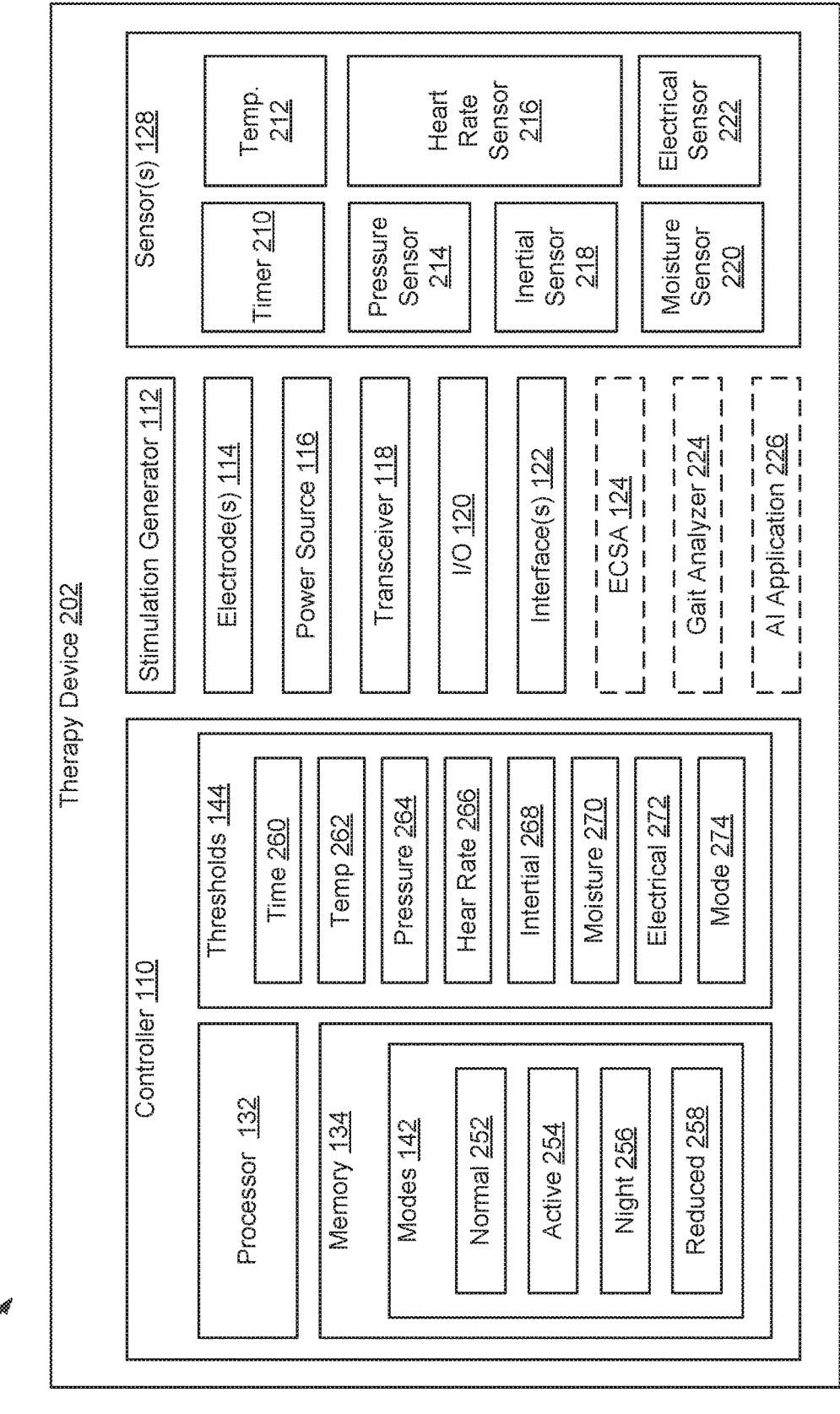
FIG. 2 is a block diagram of an example of a therapy device of a therapy system.

FIG. 2 illustrates block diagram 200 of an example of an illustrative therapy device 202 including a controller configured to operate the therapy device 202 in multiple operating modes. Therapy device 202 may include or correspond to therapy device 102 and may be included in a therapy system, such as therapy system 100 of FIG. 1.

Therapy device 202 includes many similar components to therapy device 102 of FIG. 1, which are denoted by like numbers 110-142. As illustrated in the example of FIG. 2, the therapy device 202 further includes particular modes 142 (e.g., 252-258), particular thresholds 144 (e.g., 260-274), and particular sensors 128 (e.g., 210-222).

The therapy device 202 is coupled to the tissue site of the patient by the electrically conductive adhesive (ECA) 124. Therapy device 102 may be controlled by remote device (e.g., 104, not shown) similar therapy device 102 of FIG. 1. In other examples, the therapy device 202 is controlled internally, i.e. by a control device that is integrated into therapy device 202.

As illustrated by the example of FIG. 2, therapy device 202 includes four modes (operating modes), a normal mode 252, an active mode 254, a night mode 256, and a reduced mode 258. A normal mode 252 may be a default or standard operating mode of the therapy device or set by a care provider. The active mode 254 may be a mode that is triggered by physical activity and/or a user input. For example, sensor data and corresponding thresholds may be used to determine that a patient is being active. The active mode 254 may alter therapy as compared to the normal mode 252 to account for physical exertion, increased blood flow, and/or used of the tissue site or area (e.g., use of the muscles of the area). As an illustrative example, the active mode 254 may provide reduce intensity therapy or no therapy. The therapy device 202 may still monitor sensor data to determine when to exit the active mode 254.

The night mode 256 may be a mode that is triggered by physical activity (lack of activity) and/or a user input. For example, sensor data and corresponding thresholds 144 may be used to determine that a patient is sleeping or resting. The night mode 256 may alter therapy as compared to the normal mode to account for sleeping and/or, reduced blood flow and temperature. As an illustrative example, the night mode 256 may provide reduced intensity therapy or no therapy. The therapy device 202 may still monitor sensor data to determine when to exit the night mode 256.

The reduced mode 258 (e.g., break mode) may be a mode that is triggered by conditions and/or a user input. For example, a user input may be received that indicates a user wishes to enter into the reduced mode 258, and conditions and corresponding thresholds may be used to determine that a patient still has a time or instances that can be spent in the reduced mode 258. The reduced mode 258 may alter therapy as compared to the normal mode 252 to give a user a break from therapy. As an illustrative example, the reduced mode 258 may provide reduced intensity therapy or no therapy. The therapy device 202 may still monitor sensor data to determine when to exit the reduced mode 258.

In the example illustrated in FIG. 2, therapy device 202 includes a plurality of thresholds 144, such as a time threshold 260, a temperature threshold 262, a pressure threshold 264, a heart rate threshold 266, an inertial threshold 268, a moisture threshold 270, an electrical threshold 272, a mode threshold 274, or a combination thereof. The thresholds 144 may include or correspond to conditions or values for entering a particular mode of the modes 142.

Each mode of the modes 142 may have one or more corresponding thresholds 144, one or multiple of which may be satisfied to enter the particular mode.

As illustrated by the example of FIG. 2, therapy device 202 includes multiple sensors 128, such as a timer 210, a temperature sensor 212, a pressure sensor 214, a heart rate sensor 216, an inertial sensor 218, a moisture sensor 220, an electrical sensor 222, or a combination thereof. Sensors 128 may be used to determine a mode and sensor data generated therefrom may be indicative a mode when compared to thresholds 144.

The timer 210 may be configured to determine an operational time of the therapy device 202, and may determine the time spent in each mode. The temperature sensor 212 may include or correspond to contact temperature sensors (e.g., thermometer or thermocouple) or an optical temperature sensor. Multiple temperature sensors 212 may be used to produce a differential temperature indicative a difference in temperature from the tissue site (e.g., wound or ailment) to a control site. The temperature differential may indicate a profusion level or infection of the tissue site.

The pressure sensor 214 may be configured to determine a pressure of the stimulation generator 112 (e.g., pump, for example a head pressure thereof) or a pressure of an inflatable member used to provide compression therapy. Heart rate sensor 216 may be configured to determine a heart rate or rhythm. Additionally, or alternatively, heart rate sensor 216 may include a pulse rate sensor or pulse oxygenation sensor. As an illustrative, non-limiting example, an optical pulse rate sensor may be used. To illustrate, a green laser (e.g., green LED) may emit light and a reflection of the light may be used to identify the pulse rate or pulse properties based on Doppler shift. As another illustration, a red light is emitted and scattering of the red light may be used to identify the pulse rate or pulse properties based on the differences in light scattering by an oxygen concentration of blood cells.

The inertial sensor 218 may include an accelerometer and/or gimbal. The moisture sensor 220 may include or correspond to a skin hydration sensor. The electrical sensor 222 may include or correspond to a current draw sensor or drive voltage sensor configured to determine a load on the stimulation generator 112 and/or electrodes 114 or a drive voltage applied to the stimulation generator 112. A current draw sensor or load sensor may indicate the device has been removed, such as by indicating a low load or no load (e.g., "open circuit') or may indicate misplacement, such as by indicating an abnormal or changing load.

Gait analyzer 224 includes or corresponds to a program and/or instructions for determining if a person is walking, jogging, running, going up stairs, or a combination thereof. Gait analyzer 224 may be configured to determine a person's gait and classify the person's gait based on inertial sensor data and/or inertial thresholds.

AI application 226 includes or corresponds to a program and/or instructions for implementing artificial intelligence operations. The AI application 226 may be configured to evaluate sensor data based on correlations and/or conditions derived from AI operations. The AI application 226 may be used by the gait analyzer 224 to determine or classify a gait, update inertial thresholds, update gait thresholds, or combination thereof. Additionally, or alternatively, the AI application 226 may be used update one or more thresholds, to determine a mode, or a combination thereof.

FIG. 3 illustrates block diagram 300 of an example of an illustrative remote device 304 including a controller configured to operate a therapy device (e.g., 102 or 202) in multiple operating modes. Remote device 304 may include or correspond to remote device 104 and may be included in a therapy system, such as therapy system 100 of FIG. 1. In some implementations, remote device 304 includes or corresponds to a remote device of the patient. In other implementations, the remote device 304 includes or correspond to remote device of a care provider.

Remote device 304 includes many similar components to remote device 104 of FIG. 1, which are denoted by like numbers 162-170. As illustrated in the example of FIG. 3, the remote device 304 further includes particular sensors 170, such as an accelerometer 310 and a gyroscope 312, and optionally includes the gait analyzer 224 and AI application 226 of FIG. 2. The accelerometer 310 and the gyroscope 312 may include or correspond to advanced inertial sensors or inertial sensors with increased precision or capabilities (e.g., directional movement capabilities), as compared to an inertial sensor of the therapy device.

In some implementations, the remote device 304 includes one or more of the particular modes 142 (e.g., 252-258), the particular thresholds 144 (e.g., 260-274), or the particular sensors 128 (e.g., 210-220) of FIG. 2, in addition to or in the alternative of the therapy device.

Some mobile devices, such as smart phones, include a suite of sensors used for operation of the mobile device and advanced processors. A therapy system may leverage these existing sensors and increased processing power, as compared to many conventional therapy devices and controllers, to perform complex analysis, such as gait analysis or AI operations. Such a distributed system may enable enhanced control operations with adding cost, complexity, size, and/or power requirements to the therapy device.

In implementations where remote device 304 corresponds to a device associated with the patient, such as a smartphone of the patient, the remote device 304 may transmit inputs and/or sensor data to the therapy device and the remote device 304 may receive notifications and/or updates from the therapy device.

In implementations where the remote device 304 corresponds to a device associated with a care provider, such as a computer, tablet, laptop, server, or smartphone of a doctor etc., the remote device 304 may receive log data of therapy device from the therapy device or the patient's remote device 304. The remote device 304 may transmit notifications and/or adjustments to the therapy device. For example, the remote device 304 may adjust conditions, thresholds, therapy parameters, or a combination thereof. The remote device 304 may approve or deny requests for break or reduced operating modes and/or enable remote monitoring.

As an illustrative example, the remote device 304 and/or a therapy device (e.g., 102, 202) may receive a user input indicating a request to enter a break operating mode, determine a count value of break operating modes, compare the count value to a break operating mode threshold, and determine whether to enter the break operating mode based on comparing the count value to the break operating mode threshold.

As another illustrative example, the remote device 304 and/or a therapy device (e.g., 102, 202) may receive a user input indicating a request to enter a reduced intensity operating mode, determine a duration of time spent in the reduced intensity operating mode, compare the duration to a reduced intensity operating mode threshold, and determine whether to enter the reduced intensity operating mode based on comparing the duration to the reduced intensity operating mode threshold.

As yet another illustrative example, the remote device 304 and/or a therapy device (e.g., 102, 202) may receive a skin hydration data from a moisture sensor, receiving current draw data from a current sensor, and determine whether the device is incorrectly positioned or has been removed based on the skin hydration data, the current draw data, and one or more thresholds.

As another illustrative example, the remote device 304 and/or therapy device (e.g., 102, 202) may receive from a pulse rate sensor of the therapy device, pulse rate data indicating a pulse rate of the user, determine a pulse rate threshold based on the activity indicated by the activity data, determine whether the pulse rate data satisfies the pulse rate threshold, and operating the stimulation generator in the second operating mode at least responsive to determining whether the pulse rate data satisfies the pulse rate threshold.

As yet another illustrative example, the remote device 304 and/or a therapy device (e.g., 102, 202) may receive, from a remote device, second sensor data indicating second activity by the user, compare the second sensor data to a second activity threshold; and responsive to determining that the second activity is greater than the second activity threshold, operate the stimulation generator in a third operating mode, the third operating mode associated with a third therapy parameter, where the third therapy parameter is less than the second therapy parameter.

As yet another illustrative example, the remote device 304 and/or a therapy device (e.g., 102, 202) may receive first temperature data from a first temperature sensor coupled to the tissue site, receive second temperature data from a second temperature sensor coupled to a second tissue site, determining a temperature difference (e.g., temperature differential) based on the first temperature data and the second temperature data, and compare the temperature difference to a temperature threshold to determine whether the tissue site has an infection.

FIGS. 4A-4B each illustrate views of an example of a therapy device 402, such as a therapy device for providing therapy to a leg of a user. For example, the therapy device 402 may be attached to calf of a patient and provide therapy to a calf muscle of the patient. The therapy device 402 may include or correspond to therapy device 402 as described herein and referenced in FIG. 1. FIG. 4A shows a top/front view of therapy device 402, and FIG. 4B shows a bottom/back view of therapy device 402. In the example of FIGS. 4A and 4B, therapy device 402 includes a body 404, a stimulation generator 412, electrodes 414, a power source 416, and ECA 424. Components 412-424 may include or corresponds to components 112-124 of FIG. 1, respectively.

Referring to FIG. 4A, the illustration shows a top/front view of a first side (e.g., front or top side) of therapy device 402. In FIG. 4A, body 404 is depicted and body 404 includes or corresponds to an enclosure and one or more retaining or securing devices, such as straps, bands, clips, etc. As illustrated in FIG. 4, therapy device 410 has body 404 that includes a housing 432 and two straps 434 each extending from the housing 432. One or more of straps 434 may include or correspond to a compound film and may include or be configured to receive ECA 424.

In some implementations, therapy device 410 includes an indicator 442 capable of communicating visual and/or auditory information (e.g., a light indicator to show whether the therapy device 410 is receiving power, providing therapy, positioned correctly, etc.). In some implementations, therapy device 410 includes a power switch 444 configured to of communicate with a power source 416 (illustrated in FIG. 4B). For example, power switch 444 may be configured to generate power on/power off signals. The signals may be sent to a processor or controller (e.g., 114) of therapy device 402 to control power source 416 in some implementations. In other implementations, the signals control a power delivery switch of power source 416.

In some implementations, therapy device 402 may further include one or more switches configured to communicate with therapy device 402, such as a controller thereof (e.g., 114) and/or the stimulation generator 412. In the example of FIG. 4A, therapy device 402 includes a first switch 446 and a second switch 448. Switches 446 and 448 may adjust an indication level (e.g., volume of an audio indicator) and/or adjust a level of a setting of therapy, such as current, voltage, pulse rate, etc. of the therapy.

In some implementations, therapy device 402 includes an indicator capable of providing and/or displaying information (e.g., a logo, a description, instructions). In some implementations, therapy device 402 includes an indicia 450. Indicia 450 may include a pattern, description, or other identifying information relating to the therapy device 402, any components of therapy device 402, or any component used in the process of activating or using therapy device 402.

Referring to FIG. 4B, FIG. 4B illustrates a bottom/back view of a second side (e.g., bottom or back side) of therapy device 402. FIG. 4B depicts the electrodes 414, the power source 416, and the ECA 424. The ECA 424 can have an open circuit configuration on the therapy device 402, as shown in FIG. 4B. To illustrate, therapy device 402 has multiple sections of ECA 424 and one or more of the sections are separate from another section. Additionally or alternatively, ECA 424 may further include one or more non-conductive components to separate conductive sections or portions of ECA 424.

In some implementations, therapy device 402 includes an indicia 452, similar to indicia 450. Indicia 452 may also include a pattern, description, or other identifying information relating to the therapy device 402, any components of therapy device 402, or any component used in the process of activating or using therapy device 402. Such indicia 450, 452 may be used to indicate how to use or align therapy device 402.

Figures 5A, 5B:
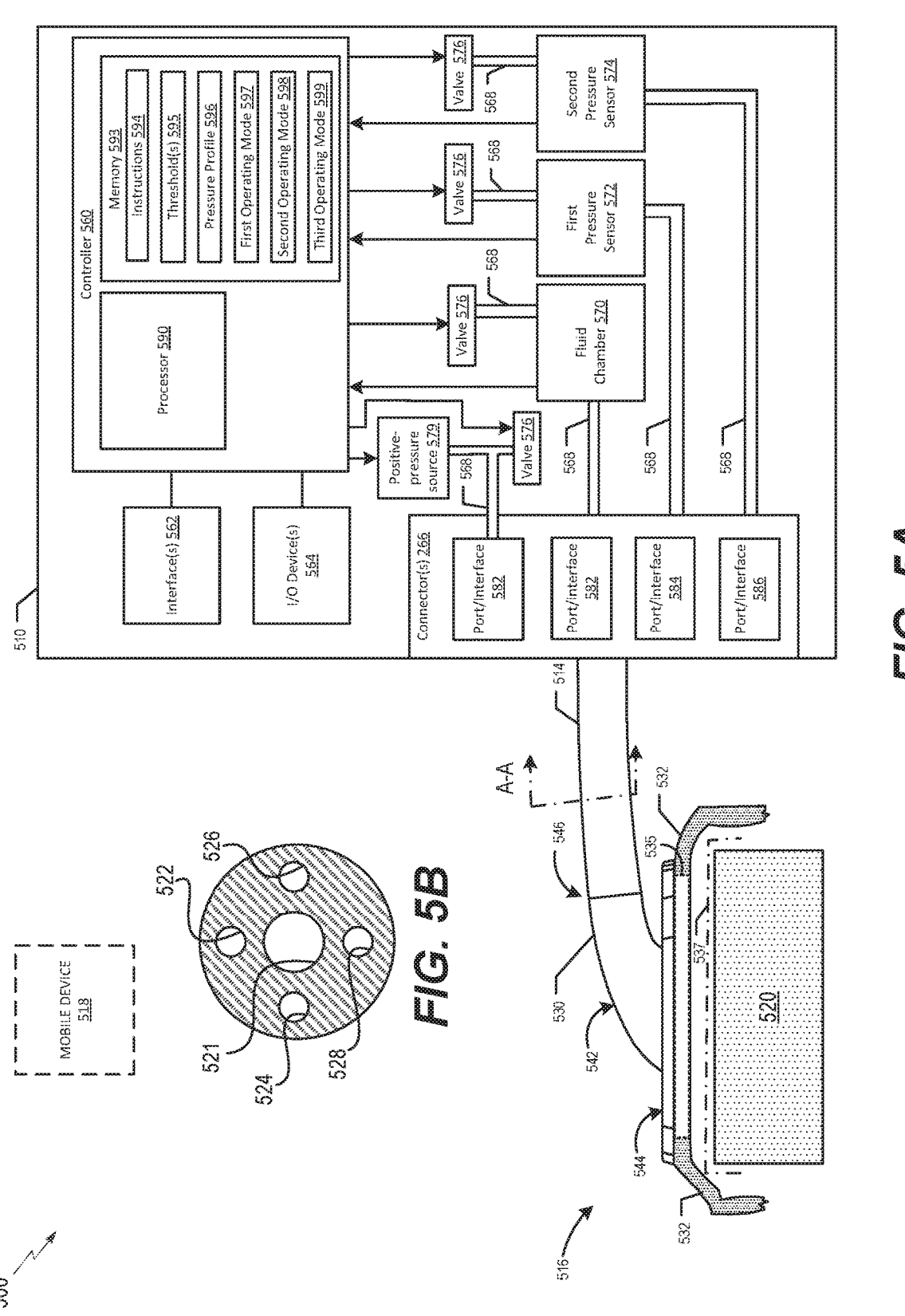
FIG. 5A is a diagram of an example of another system for compression therapy.
FIG. 5B is a cross-sectional view of an example of a tube taken along line A-A of FIG. 5A.

Referring to FIG. 5A, an illustrative example of an illustrative system 500 (e.g., a compression therapy system) is shown. System 500 includes a compression therapy device 510, a tube 514, and a dressing 516. System 500 may optionally include a mobile device 518. Dressing 516 is coupled to device 510 via tube 514. Device 510 may include or correspond to therapy device 102.

Referring to FIG. 5B, an illustrative example of a cross-section of tube 514 (when tube 514 comprises multiple lumens) along line A-A of FIG. 5A is shown. Tube 514 may include a primary lumen 521 (e.g., compression lumen) and one or more secondary lumens, such as a first secondary lumen 522 (e.g., a return or bleed lumen), a second secondary lumen 524 (e.g., a first sense lumen), a third secondary lumen 526 (e.g., a second sense lumen), and a fourth secondary lumen 528 (e.g., a third sense lumen). Although described as having a single primary lumen (e.g., 521), tube 514 may have multiple primary lumens. Although tube 514 has been described and/or shown as having a circular cross-sectional shape, in other implementations, tube 514 may have a cross-sectional shape other than a circle, such as an oval, triangle, quadrilateral, pentagon, star, or another shape, as illustrative, non-limiting examples.

Dressing 516 (e.g., a compression dressing or compression wrap) is configured to be coupled to (e.g., adhered to) a tissue site 520 of a patient. Dressing 516 may include one or more components, such as a connector 530 and an inflatable member 532, as illustrative, non-limiting examples. Inflatable member 532 may be coupled to connector 530, and may include an opening 535 (e.g., an aperture) to enable communication (e.g., fluid communication) between connector 530 and inflatable member 532.

As shown, inflatable member 532 is coupled to tissue site 520 via a representative adhesive 537, such as a medically acceptable, pressure-sensitive adhesive that extends about a periphery, a portion, or an entirety of inflatable member 532. Additionally, or alternatively, inflatable member 532 may be coupled to tissue site 520 via a double-sided drape tape, paste, hydrocolloid, hydrogel, and/or other sealing device or element, as illustrative, non-limiting examples. In other implementations, the dressing 516 is coupled to the tissue site by compression, e.g., a compression sleeve secure the dressing 516 in place, or mechanical means, such as hooks, belts, loops, Velcro, etc.

Connector 530 may include a connector body 542, a base 544, and an interface 546 (e.g., a port). Connector body 542 may include correspond to housing of connector 530 and base 544 may define or correspond to interface 246. Interface 546 is configured to be coupled to tube 514.

Tube 514 includes one or more lumens. For example, tube 514 may include a compression lumen (e.g., 521), a release lumen, and one or more sense lumens. As shown, a first end of tube 514 is coupled to dressing 516 and a second end of tube 514 is coupled to device 510. In some implementations, the second end of tube 514 may include a therapy device connector configured to couple (e.g., mate) with device 510.

Device 510 includes a controller 560, one or more interfaces 562, one or more I/O devices 564, and one or more connectors, such as a representative connector 566. Device 510 further includes one or more conduits 568, a fluid chamber 570, pressure sensors 572, 574, one or more valves 576 (e.g., solenoid valves), and a positive-pressure source 579.

Connector 566 is configured to be coupled to tube 514, such as the second end of tube 514. Connector 566 includes one or more ports/interfaces, such as a first port/interface 580, a second port/interface 582, a third port/interface 584, a fourth port/interface 586. When connector 566 is coupled to tube 514, the compression lumen (e.g., 521) is in fluid communication with first port/interface 580, the release lumen (e.g., 522) is in fluid communication with second port/interface 582, first sense lumen (e.g., 524) is in fluid communication with third port/interface 584, and second sense lumen (e.g., 526) is in fluid communication with fourth port/interface 586.

Each of first port/interface 580, second port/interface 582, third port/interface 584, and fourth port/interface 586 is coupled to one or more components of device 510 via one or more conduits (e.g., 568). For example, first port/interface 580 is coupled to positive-pressure source 579, second port/interface 582 is coupled to fluid chamber 570 (e.g., a canister or a liquid-collection cavity), third port/interface 584 is coupled to a first pressure sensor 572, and fourth port/interface 586 is coupled to a second pressure sensor 574. The pressure sensors 572, 574 may be configured to generate data indicative of pressure within dressing 516. Although described as having two pressure sensors (e.g., 572, 574), in other implementations, device 510 may include fewer than two pressure sensors, such as no pressure sensors or a single pressure sensor, or more than two pressure sensors. Additionally, each of first port/interface 580, second port/interface 582, third port/interface 584, and fourth port/interface 586 is coupled to a corresponding valve (e.g., 576), such as a solenoid valve, which is configured to change pressure from dressing 516. First port/interface 580 is coupled to positive-pressure source 579 and a corresponding valve 576 via a conduit 568.

In some implementations, device 510 includes positive-pressure source 579 that is configured to provide positive-pressure to inflatable member 532 of dressing 516 such that inflatable member 532 is expanded, and/or positive-pressure is applied to at least target tissue 536. Positive-pressure source 579 (e.g., stimulation generator 112) may include a mechanically and/or electrically-powered device, such as a manually-actuated or manually-charged pump, an oxygen tank, an oxygen collector, a wall port, a micro-pump, a disc-pump, and/or the like, as illustrative, non-limiting examples.

Controller 560 includes a processor 590 coupled to a memory 593 (e.g., a computer-readable storage device). Memory 593, such as a non-transitory computer-readable storage medium, may include volatile memory devices (e.g., random access memory (RAM) devices), nonvolatile memory devices (e.g., read-only memory (ROM) devices, programmable read-only memory, and flash memory), or both. Memory 593 may be configured to store instructions 594, a pressure profile 596, and one or more thresholds 595. Instructions 594 may be configured to, when executed by the one or more processors 590, cause the processor(s) 590 to perform one or more operations.

Pressure profile 596 may include desired target pressures to be provided to a patient over a time period. In some implementations, the pressure profile 596 may include a set-up profile applying target pressures at the commencement of therapy treatments and a maintenance profile for applying target pressure during therapy. One or more thresholds 595 may include one or more one or more pressure thresholds, one or more time thresholds, one or more operating mode thresholds, one or more sensor data thresholds, one or more other thresholds (e.g., 144), or a combination thereof.

Processor 590 may include a microcontroller/microprocessor, a central processing unit (CPU), a field-programmable gate array (FPGA) device, an application-specific integrated circuits (ASIC), another hardware device, a firmware device, or any combination thereof. Processor 590 may be configured to execute instructions 594, execute and/or operate according to pressure profile 596, and/process sensor data generate by pressure sensors 572, 574. For example, processor 590 may be configured to process sensor data (e.g., pressure signals) received by one or more sensors (e.g., 572, 574) and/or monitor the sensor data. Additionally, or alternatively, processor 590 may be configured to issue one or more alerts according to a pre-determined pressure therapy (e.g., pressure profile 596) for a patient and/or based on one or more thresholds 595. In some implementations, the one or more alerts may be in the form of a visual alert (e.g., a light indicator), a tactile alert, an audible alert, a message presented via a display, or a message transmitted to another device. In the event that processor 590 determines that pressure profile 596 is being implemented, processor 590 may provide an indication that the sensor data (e.g., the monitored pressure at dressing 516) is following pressure profile 596. For example, processor 590 may initiate a visual indication (e.g., a light indicator), a tactile indication, an audible indication, a message presented via a display, or a message transmitted to another device.

The one or more interfaces 562 may include a wired interface, a wireless interface, or both. In some implementation, the one or more interfaces 562 may include a network interface and/or a device interface configured to be communicatively coupled to one or more other devices. For example, interfaces 562 may include a transmitter, a receiver, or a combination thereof (e.g., a transceiver), and may enable wired communication, wireless communication, or a combination thereof. Additionally, or alternatively, the one or more interfaces 562 may include serial interfaces (e.g., universal serial bus (USB) interfaces or Institute of Electrical and Electronics Engineers (IEEE) 1394 interfaces), parallel interfaces, display adapters, audio adapters, and other interfaces. The one or more I/O devices 564 may include a mouse, a keyboard, pointing devices, a display device, the camera, speakers, microphones, touch screens, other I/O devices, or a combination thereof. Processor 590 may be configured to send and/or receive data via the interface(s) 562 and/or the I/O device(s) 564.

During operation, dressing 516 is coupled to tissue site 520 so as to cover target tissue 536. Additionally, dressing 516 is coupled to device 510 via tube 514. In some implementations, processor 590 receives an input via I/O device(s) 564, such as a touchscreen, to select a pressure profile (e.g., 596) of multiple pressure profiles stored at memory 593, to initiate positive-pressure therapy, or both. Alternatively, the input may indicate a value of a positive-pressure to be provided and/or maintained. Responsive to the input, controller 560 (e.g., processor 590) generates one or more commands to initiate operations of one or more components of device 510. For example, processor 590 may access pressure profile 596 (e.g., a set-up profile or a maintenance profile). Additionally, or alternatively, processor 590 may activate and/or regulate positive-pressure source 579, one or more valves 576, or both. In some implementations, processor 590 may control operation of positive-pressure source 579, one or more valves 576 based on at least in part on the input (e.g., the pressure profile 596 selection or the value of the pressure).

In some implementations, valve 576 coupled to first pressure sensor 572 may be operated independent of valve 576 coupled to second pressure sensor 574. For example, controller 560 may operate valve 576 coupled to first pressure sensor 572 based on sensor data received from first pressure sensor 572 and/or based on a first set of one or more thresholds (e.g., 595). Controller 560 may operate valve 576 coupled to second pressure sensor 574 based on sensor data received from second pressure sensor 574 and/or based on a second set of one or more thresholds (e.g., 595). The first set of one or more thresholds and the second set of one or more thresholds may include one or more of the same threshold value(s) and/or one or more different threshold value(s). Additionally, or alternatively, in other implementations, controller 560 may operate one or more of the valves based on an average of sensor data of two or more sensors. For example, controller 560 may control one or more valves, such as the valve coupled to positive-pressure source 579 based on an average of the sensor data (received from pressure sensors 572, 574) and a third set of one or more thresholds. The third set of one or more thresholds may include one or more of the same threshold value(s) and/or one or more different threshold value(s) as the first set of one or more thresholds and/or the second set of one or more thresholds.

Positive-pressure provided by positive-pressure source 579 via tube 514 can cause pressurized fluid to be provided to inflatable member 532 via tube 514 (e.g., positive-pressure/fluid lumen) and first port/interface 580. In some implementations, device 510 may include a sensor and/or regulator (not shown) coupled to controller 560 (e.g., processor 590) and configured to monitor a pressure of the positive-pressure source 579 or the corresponding conduit 568 thereof. For example, processor 590 may receive sensor data from the sensor that indicates a pressure level of the regulator and may operate valve 576 to control a pressure and/or volume of positive-pressure source 579. Once a desired pressure of fluid is achieved, the pressurized fluid may be provided to inflatable member 532 to provide compression therapy to target tissue 520.

In some implementations, controller 560 (e.g., processor 590) is configured to operate a pump (e.g., stimulation generator 112, positive-pressure source 579, or a combination thereof) in multiple operating modes. As illustrated in FIG. 5A controller 560 (e.g., processor 590) the configured to operate positive-pressure source 579 in one of at least three different operating modes. The at least three operating modes include a first operating mode 597 (a "operating mode"), a second operating mode 598 (a "reduced power operating mode"), and a third operating mode 599 (a "sleep operating mode"). The different operating modes may be associated with different drive voltages of the pump and/or different duty cycle ranges of the pump. In other implementations, the controller 560 (e.g., processor 590) is configured to operate positive-pressure source 579 in two operating modes or four or more operating modes. As illustrative examples, the two operating modes may include the normal operating mode and the reduced power operating mode or the normal power operating mode and the sleep operating mode. As an additional example, the four or more operating modes may include the normal power operating mode, a first reduced power mode (e.g., light activity), a second reduced power mode or sleep mode (e.g., heavy activity and/or resting/night time), and a break mode.

During operation, controller 560 may initiate transmission of a notification, a low battery alert, or both, to mobile device 518. Additionally, or alternatively, the pump (e.g., stimulation generator 112 and/or positive-pressure source 579) or device 510 may include one or more indicators, such as lights, and a mode alert, an activity alert, a low power alert, or a combination thereof, may be initiated by controller 560 turning on one or more of the indicators (or issuing another type of notification, such as an audible notification, a haptic notification, etc.). Although a compression device is illustrated in FIG. 5A, in other implementations, therapy may be provided by a mechanical device, such as massage head.

Thus, FIG. 5A describes system 500 for providing compression therapy. System 500 may advantageously operate a pump (e.g., positive-pressure source 579) in one of at least two operating modes to improve the flexibility of system 500. For example, operating the pump in second operating mode 598 (e.g., the activity mode) provide enhanced patient comfort and effectiveness when the patient is active.

Figure 6:
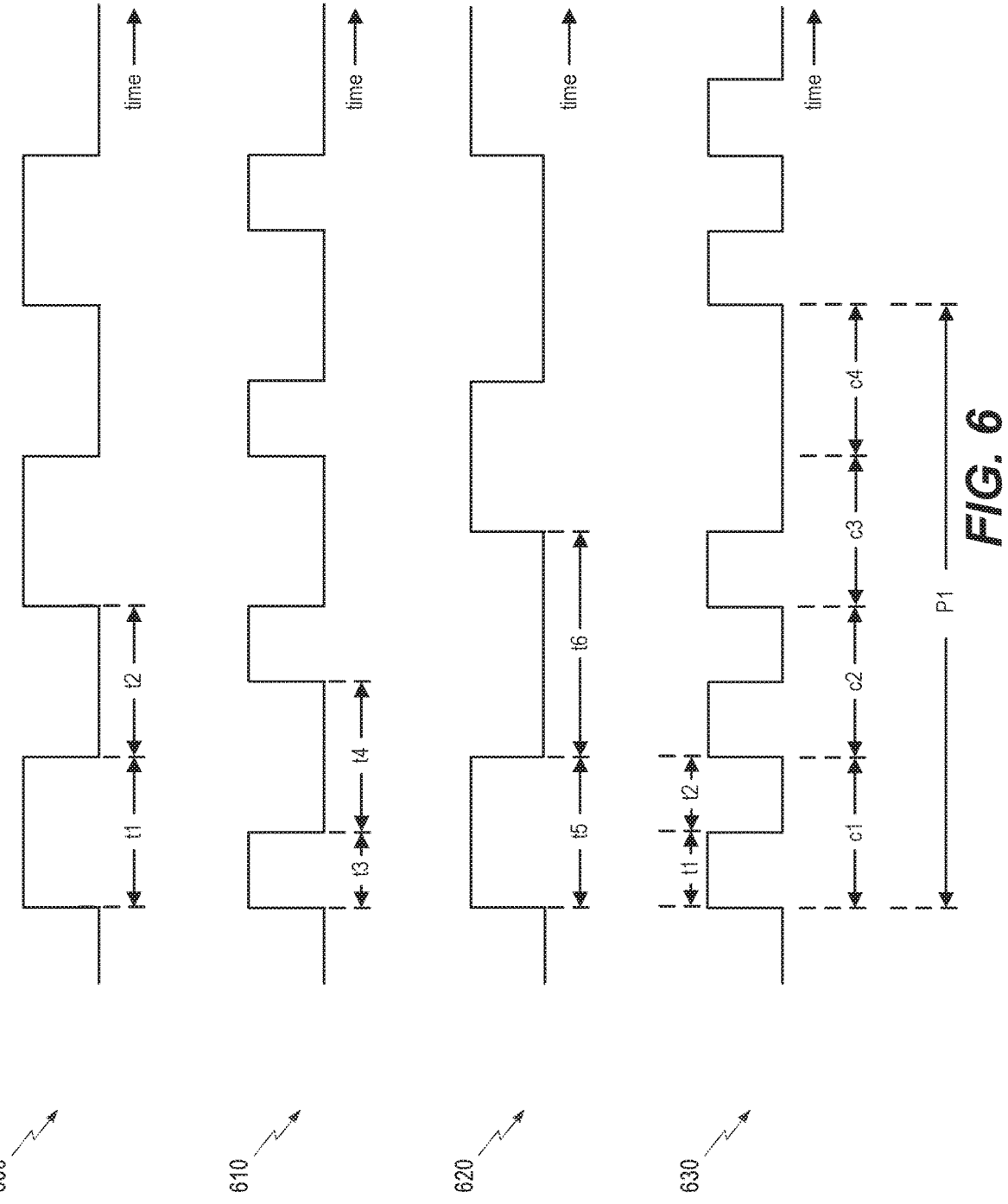
FIG. 6 is a diagram of examples of changing a duty cycle of a stimulation generator of a therapy device.

FIG. 6 illustrates examples of adjusting (e.g., decreasing) a duty cycle of a therapy device, as stimulation generator 112 and/or positive-pressure source 579. The duty cycle of the therapy device may be decreased when the therapy device is transitioned from one operating mode to another operating mode, such as from a normal power operating mode to a reduced power operating mode. Although the changes are illustrated as decrements to the duty cycle, the duty cycle may be increased, such as when transitioning from one operating mode to another operating mode, such as from a reduced power operating mode to a normal power operating mode. A voltage may also be adjusted (e.g., increased) in addition to adjusting (e.g., increasing) the duty cycle.

FIG. 6 includes a first example 600 of a duty cycle of a therapy device, such as stimulation generator 112 or positive-pressure source 579. In first example 600, the therapy device is on (e.g., a voltage is applied to electrodes or a drive voltage is applied to the pump) for the same amount of time each period that the therapy device is off (e.g., no voltage is applied to the electrodes or the pump). For example, the therapy device is on for a first time t1, the therapy device is off for a second time t2, and t1 is substantially equal to t2. This pattern is repeated for each period of time of the duty cycle.

FIG. 6 also includes a second example 610 of a duty cycle of the therapy device. Second example 610 has a reduced duty cycle as compared to first example 600. In second example 610, the amount of time that the therapy device is on (e.g., the "on-time" of the therapy device) is reduced. For example, the therapy device is on for a third time t3, the therapy device is off for a fourth time t4, and t3 is less than t4 (and t1 and t2). Thus, in second example 610, the amount of time that the therapy device is on is reduced (e.g., a set time or a maximum allowable on-time for a particular cycle), thereby reducing the overall duty cycle.

FIG. 6 also includes a third example 620 of a duty cycle of the therapy device. Third example 620 has a reduced duty cycle as compared to first example 600. In third example 620, the amount of time the therapy device is off (e.g., the "off-time" of the therapy device) is increased. For example, the therapy device is on for a fifth time t5 (which is the same as t1 and t2), the therapy device is off for a sixth time t6, and t6 is greater than t5 (and t1 and t2). Thus, in third example 620, the amount of time that the therapy device is off is increased, thereby reducing the overall duty cycle.

FIG. 6 further includes a fourth example 630 of a duty cycle of the therapy device. Fourth example 630 illustrates another technique for reducing the duty cycle of the therapy device-limiting the cycles per period (P1) that the therapy device is on. For example, the duty cycle of fourth example 630 includes a threshold or limit on the number of cycles (on-off cycles) that may occur during the period (P1). As illustrated in FIG. 6, a cycle has a time of c (e.g., c1, c2, c3, etc.) and the on and off times are equal (t1=t2), similar to the first example 600. In FIG. 6, the threshold or limit is illustrated has having a value of three cycles within period (P1) and period (P1) is illustrated as four cycles in duration. By reducing the number of cycles (e.g., the number of cycles that the therapy device is on), the duty cycle of the therapy device may be reduced. Although limiting a number of cycles over a duration or period is illustrated in the fourth example 630, in other examples, a threshold number of continuous cycle before a delay or cooling of period (duration of c4) may be used to control or adjust duty cycles.

Although FIG. 6 illustrates distinct examples (600-630) of reducing the duty cycle of the therapy device, one or more of the examples may be combined. For example, the on-time of the therapy device may be reduced and the off-time of the therapy device may be increased. Additionally, or alternatively, the on-time may be reduced and the number of cycles may be limited. Thus, any combination of the techniques described with reference to FIG. 6 may be used to reduce the duty cycle of the therapy device. Additionally, reversing the techniques may be used to increase the duty cycle of the therapy device. For example, the on-time may be increased, the off-time may be reduced, and/or the number of cycles may be increased to increase the duty cycle.

FIG. 7 illustrates a method 700 of using a wound therapy device. Method 700 includes applying a therapy device, at 710. For example, the therapy device may include or correspond to the therapy 102, 202, 402 or dressing 516. The therapy device may be applied to a tissue site of a user. Method 700 includes turning the therapy device on, at 712. For example, a power switch may be toggled into an on position.

Method 700 includes applying therapy, at 714. For example, a controller (e.g., 110, 560) of the device 210 may stimulation generator 112 or positive-pressure source 579 to apply pressure (e.g., positive pressure) to the wound site. Applying the therapy may include the controller 110 operating stimulation generator 112 in one or more different operating modes, as further described with reference to FIGS. 8-11.

Method 700 includes turning the device off, at 716. For example, when therapy is complete, the therapy device may be turned off, such as be toggling a power switch into an off position. Method 700 further includes removing the therapy device, at 718. For example, the dressing may be detached from the tissue site and the therapy device may be disconnected from the dressing.

Figure 8:
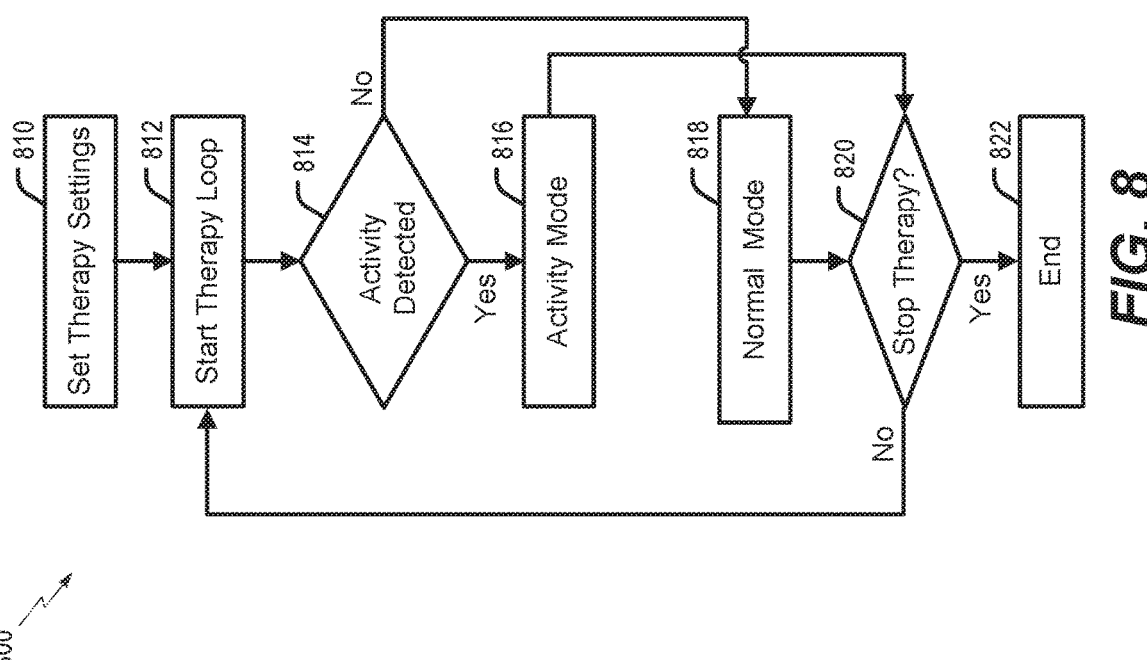
FIG. 8 is a flowchart illustrating an example of a method of operating a stimulation generator of a therapy device in an activity operating mode.

FIG. 8 illustrates a method 800 of operating a therapy device in one of multiple operating modes. In a particular implementation, method 800 is performed by controller 110. In a particular implementation, method 800 corresponds to operation 714 of FIG. 7.

Method 800 may optionally include setting therapy settings, at 810. For example, a controller (e.g., 110, 560) may load a set of pre-stored settings from a memory. Additionally, or alternatively, the settings may be received from a user (e.g., via a user input device or a separate mobile device, such as a cell phone). Method 800 includes starting the therapy loop, at 812. For example, the controller (e.g., 110, 560) may load (or receive) the settings and start the loop when the therapy device is powered on.

Method 800 also includes determining whether activity of the patient is detected or determined, at 814. For example, in some implementations, the therapy device may include one or more inertial sensors and/or activity detection logic, such as gait analyzer 224 or AI application 226. In such implementations, the controller may determine whether the therapy device is moving, and this whether the patient attached to the therapy device is moving.

If activity is detected, method 800 proceeds to 816, and an activity or active operating mode is initiated. For example, the controller may send one or more control signals to therapy device 102 to operate stimulation generator 112 in an active operating mode. The active operating mode may be associated with a first therapy settings of stimulation generator 112. The active operating mode may enable a therapy device to be more comfortably used while the patient is active.

Returning to 814, if activity is not detected, method 800 proceeds to 818, and the normal operating mode is initiated. For example, the person may not be active and thus normal therapy may be applied.

Method 800 then continues to 820, and it is determined whether to stop therapy. For example, one or more conditions may be evaluated for determining whether to stop therapy. To illustrate, the therapy device may evaluate a timer, a counter, if a user input is received, if a remote input is received, or a combination thereof, to determine if therapy should be stopped.

If it is determined if therapy is to stop, method 800 proceeds to 822, and method 800 terminates at 822. For example, the controller may detect that a user has pressed a stop button on the therapy device. Alternatively, if it is determined that therapy is not to stop, method 800 returns to 812, and the loop begins again.

Thus, method 800 enables a controller to operate a stimulation generator of a therapy device in an activity mode based on activity data from one or more sensors, including sensors of the therapy device or remote sensors. For example, sensor data from an accelerometer of the patient's phone or step counter may be used to determine activity. As another example, inertial sensors, pulse rate sensors, temperature sensors, and/or motion sensors of the therapy device may be used individually or in combination to determine activity. Thus, method 800 enables operation (e.g., reduced intensity operation) of the therapy device while a patient is active or temporarily ceasing therapy while the patient is active.

Figure 9:
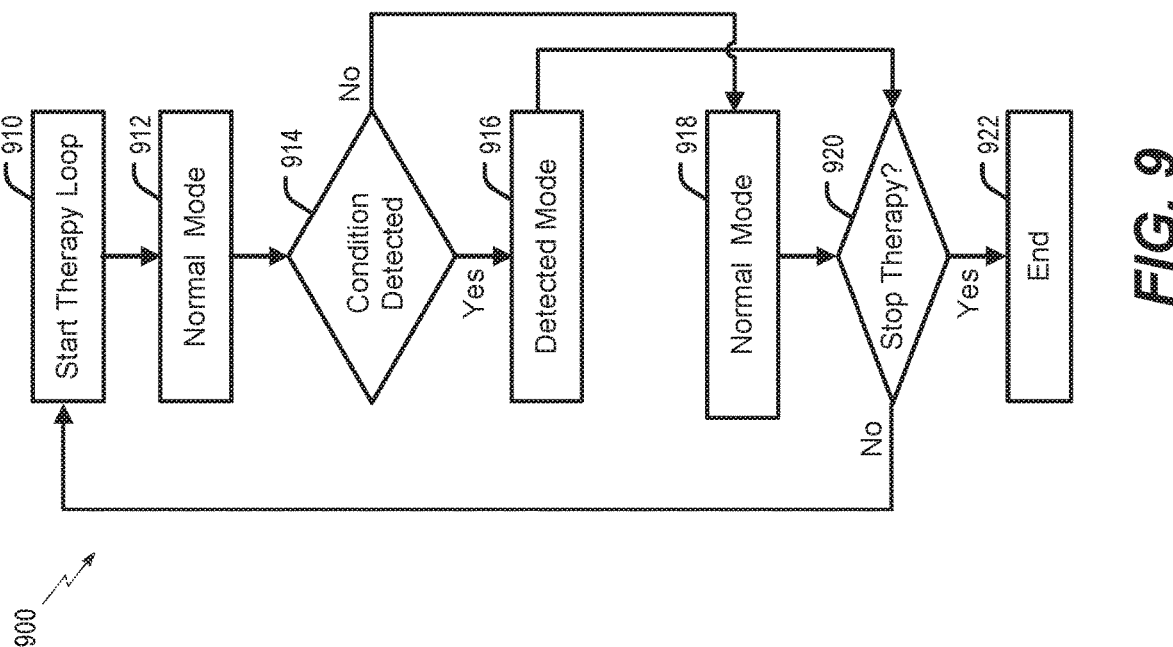
FIG. 9 is a flowchart illustrating an example of a method of operating a stimulation generator of a therapy device in one of multiple operating modes.

FIG. 9 illustrates a method 900 of operating a therapy device in one of multiple operating modes. In a particular implementation, method 900 is performed by therapy device 102, controller 110, remote device 104, therapy device 202, remote device 304, therapy device 402, or controller 560. In a particular implementation, method 900 corresponds to operation 714 of FIG. 7.

Method 900 includes starting the therapy loop, at 910. For example, a controller (e.g., 110, 560) may load (or receive) settings and start the loop when the therapy device is powered on. Method 900 includes activating a normal mode (or default mode), at 912. For example, the controller (e.g., 110, 560) may select and/or activate a normal or startup mode response to power on and/or starting the therapy loop.

Method 900 also includes determining one or more conditions, at 914. As illustrative, non-limiting examples, the controller (e.g., 110, 560) may compare sensor data and/or inputs to the thresholds to determine if one or more conditions are satisfied. The conditions may include an activity condition as in FIG. 8, a sleep condition, a mode select condition, a settings adjustment condition. In such implementations, the controller may determine a state or action based on the conditions. To illustrate, the controller may determine a sleep state and to switch to a sleep operating mode or an inactive mode. In the inactive mode, although the therapy device is not providing therapy, the device is still powered on and may optionally be receiving sensor data.

As another illustration, the controller may determine a user input has been received, such as a user input to select a reduced intensity mode or an activity mode. The controller may switch to a reduced intensity mode or an active mode responsive to the selection. In some implementations, the controller may not switch to the reduced intensity mode based on a second determining or a second condition. For example, if the user has requested more reduced intensity therapy sessions than allotted by a care provider (e.g., counter of reduced intensity therapy sessions exceeds a corresponding threshold).

As yet another illustration, the controller may determine a remote input and/or control signal has been received, such as a remote user input to adjust thresholds and/or therapy parameter settings. The controller may adjust a value of a threshold or therapy parameter responsive to the input. Alternatively, the controller may set a particular operating mode responsive to the input.

As another illustration, the controller may determine an AI input or action. To illustrate, AI application 224 may determine, based on models and sensor data, to adjust a threshold, a therapy parameter, and/or enter a particular operating mode. Thus, the therapy device may utilize machine learning to more efficiently and effectively provide therapy.

If a condition is detected at 914, method 900 proceeds to 916, and a detected operating mode or action is initiated. For example, the controller may send one or more control signals to therapy device 102 to operate stimulation generator 112 in a particular operating mode.

If a condition is not detected at 914, method 900 proceeds to 918, and the normal operating mode is resumed or initiated. For example, the person may not be active and thus normal therapy may be applied.

Method 900 then continues to 920, and it is determined whether to stop therapy. For example, one or more conditions may be evaluated for determining whether to stop therapy. To illustrate, the therapy device may evaluate a timer, a counter, if a user input is received, if a remote input is received, or a combination thereof, to determine if therapy should be stopped.

If it is determined if therapy is to stop, method 900 proceeds to 922, and method 900 terminates at 922. For example, the controller may detect that a user has pressed a stop button on the therapy device. Alternatively, if it is determined that therapy is not to stop at 920, method 900 returns to 910, and the loop begins again.

Thus, method 900 enables a controller to operate a stimulation generator of a therapy device in multiple different operating modes subject to multiple different conditions. Thus, method 900 enables more effective operation of the therapy device as the therapy device can adapt to provide more optimal therapy based on inputs, conditions, or both.

Although FIGS. 8 and 9 are illustrated as loops, in other implementations the therapy unit may operate in a serial fashion and may periodically evaluate data and make determinations.

FIG. 10 illustrates a method 1000 of operating a pump of a wound therapy device. Method 1000 may be performed at or by system 100, therapy device 202, remote device 304, therapy device 402, and/or by controller 560. Method 1000 includes identifying a power-on event of a therapy device, at 1010. The therapy device is configured to be worn by a user. For example, controller 110 of therapy device 102 may detect a power-on event.

Method 1000 also includes, responsive to the power-on event, operating a stimulation generator of the therapy device in a first operating mode, at 1012. The first operating mode is associated with a first therapy parameter. For example, controller 110 may operate stimulation generator 112 or positive-pressure source 579, or a combination thereof in first operating mode 597. In some implementations, operating the stimulation generator in the first operating mode includes sending one or more control signals indicating the first operating mode to the stimulation generator. Additionally, or alternatively, operating the stimulation generator in the first operating mode includes adjusting a voltage applied to or generated by the stimulation generator.

Method 1000 includes receiving, from a sensor of the therapy device, sensor data indicating activity by the user, at 1014. For example, controller 110 receives, from inertial sensor 220, inertia data indicating an inertia or acceleration of the user and/or the therapy device. To illustrate, the inertia or acceleration indicated corresponds to activity of the patient/user.

Method 1000 also includes determining whether the activity satisfies a first activity threshold, at 1016. For example, controller 110 may compare the activity (e.g., inertia or acceleration) to one of the one or more thresholds 595.

Method 1000 further includes, responsive to determining that the activity satisfies the first activity threshold, operating the stimulation generator in a second operating mode, at 1018. The second operating mode is associated with a second therapy parameter. The first therapy parameter is greater than the second therapy parameter. For example, controller 110 may operate stimulation generator in second operating mode 598, which is associated with a lower voltage and/or current than first operating mode 597.

Thus, method 1000 describes operating a stimulation generator of a therapy device in at least two operating modes, such as a normal mode and an activity mode. The activity mode may include or correspond to an inactive mode or a reduced intensity mode. The at least two operating modes provide benefits as compared to conventional a therapy devices that operate in a single operating mode. For example, operating in the second operating mode (e.g., the activity mode) may provide a lesser amount, but still a therapeutic amount, of therapy from the stimulation generator while the patient is active.

FIG. 11 illustrates a method 1100 of operating a pump of a wound therapy device. Method 1100 may be performed at or by system 100 or 200, and/or by controller 560. Method 1100 includes determining that a patient associated with a therapy device is in an active state, at 1110. For example, controller 110 determine that a therapy device, and the user attached thereto, are moving based on comparing sensor data to one or more corresponding thresholds. For example, inertial sensor data may indicate movement/activity. As another example, heart rate or pulse rate may indicate movement/activity. As yet another example, a temperature sensor may indicate movement/activity. The sensor data may be compared to one or more thresholds and/or processed by a gait analyzer or AI application to determine activity or an activity level of one or more activity levels.

Method 1100 further includes, responsive to determining that a patient associated with a therapy device is in an active state, transitioning the therapy device from a first operating mode to a second operating mode, where the second operating mode is an activity operating mode. For example, controller 110 may operate stimulation generator 112 or pressure source 579 in second or third operating mode 598, 599, which is associated with a therapy parameter that is different from (e.g., less than) a therapy parameter associated with first operating mode 597.

Thus, method 1100 describes operating a stimulation generator of a therapy device in at least two operating modes, such as a normal mode and an activity mode. The activity mode may include or correspond to an inactive mode or a reduced intensity mode. The at least two operating modes provide benefits as compared to conventional a therapy devices that operate in a single operating mode. For example, operating in the second operating mode (e.g., the activity mode) may provide a lesser amount, but still a therapeutic amount, of therapy from the stimulation generator while the patient is active.

One or more of the methods 700-1100 of FIGS. 7-11 may be implemented in a computer-readable storage device storing instructions that, when executed by a processor, cause the processor to perform the operations of the corresponding method.

It is noted that one or more operations described with reference to one of the methods of FIGS. 7-11 may be combined with one or more operations of another of FIGS. 7-11. For example, one or more operations of method 1000 may be combined with one or more operations of method 1100. Additionally, or alternatively, one or more operations described above with reference to FIGS. 1-3 and 5A may be combined with one or more operations of FIGS. 7-11, or a combination of FIGS. 7-11.

The above specification and examples provide a complete description of the structure and use of illustrative examples. Although certain aspects have been described above with a certain degree of particularity, or with reference to one or more individual examples, those skilled in the art could make numerous alterations to aspects of the present disclosure without departing from the scope of the present disclosure. As such, the various illustrative examples of the methods and systems are not intended to be limited to the particular forms disclosed. Rather, they include all modifications and alternatives falling within the scope of the claims, and implementations other than the ones shown may include some or all of the features of the depicted examples. For example, elements may be omitted or combined as a unitary structure, connections may be substituted, or both. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one example or may relate to several examples. Accordingly, no single implementation described herein should be construed as limiting and implementations of the disclosure may be suitably combined without departing from the teachings of the disclosure.

The previous description of the disclosed implementations is provided to enable a person skilled in the art to make or use the disclosed implementations. Various modifications to these implementations will be readily apparent to those skilled in the art, and the principles defined herein may be applied to other implementations without departing from the scope of the disclosure. Thus, the present disclosure is not intended to be limited to the implementations shown herein but is to be accorded the widest scope possible consistent with the principles and novel features as defined by the following claims. The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A control device comprising:
a processor configured to control a therapy device, the therapy device comprising:
a stimulation generator configured to provide stimulation to a tissue site;
a first electrode;
a second electrode;
a first section of electrically conductive adhesive electrically coupled with the first electrode; and
a second section of electrically conductive adhesive electrically coupled with the second electrode, the second section of electrically conductive adhesive separate from the first section of electrically conductive adhesive;
wherein the first section of electrically conductive adhesive and the second section of electrically conductive adhesive are configured to couple the therapy device to a patient; and
a memory coupled to the processor and configured to store instructions, wherein the processor is configured to execute the instructions stored at the memory to:
determine that the patient associated with the therapy device is in an active state;
transition the therapy device from a first operating mode to a second operating mode, wherein the second operating mode is an activity operating mode, wherein the activity operating mode comprises a reduced intensity stimulation operating mode as compared to the first operating mode;
receive a user input indicating a request to enter a break operating mode, wherein the break operating mode is a second reduced intensity stimulation operating mode or a paused therapy mode;
determine a count value of break operating modes in response to receiving the user input indicating the request to enter the break operating mode;
compare the determined count value of break operating modes to a break operating mode threshold; and
determine whether to enter the break operating mode based on the comparison of the determined count value of break operating modes to the break operating mode threshold.

2. The control device of claim 1, wherein the activity operating mode comprises an inactive or standby operating mode.

3. The control device of claim 1, wherein the stimulation generator is configured to provide electric stimulation therapy.

4. The control device of claim 1, wherein the stimulation generator includes a pump configured to provide compression therapy.

5. The control device of claim 1, wherein the processor is further configured to transition the therapy device to a third operating mode, wherein the third operating mode is a second activity operating mode or a night time mode.

6. The control device of claim 1, further comprising one or more sensors coupled to the processor, wherein the one or more sensors comprise an inertial sensor, a heart rate sensor, a temperature sensor, a moisture sensor, an electrical sensor, or a combination thereof, and wherein the one or more sensors are configured to generate sensor data indicating an activity level of the patient.

7. A therapy device, comprising:
a stimulation generator configured to provide stimulation therapy to a tissue site of a patient;
a first electrode;
a second electrode;
a first section of electrically conductive adhesive electrically coupled with the first electrode;
a second section of electrically conductive adhesive electrically coupled with the second electrode;
wherein the first section of electrically conductive adhesive and the second section of electrically conductive adhesive have an open circuit configuration when the first section of electrically conductive adhesive and the second section of electrically conductive adhesive are not coupled to the patient;
wherein the first section of electrically conductive adhesive and the second section of electrically conductive adhesive are configured to couple the therapy device to the patient; and
a controller coupled to the stimulation generator and configured to:
transition the stimulation generator from operating in a first operating mode to operating in a second operating mode responsive to determining that the patient is in an active state, wherein the second operating mode includes a second therapy parameter less than a first therapy parameter of the first operating mode, wherein the therapy parameters include voltage, drive voltage, current, duty cycle, compression pressure, or a combination thereof; and
transition the stimulation generator from operating in the first operating mode or the second operating mode responsive to:
receiving a user input indicating a request to enter a break operating mode;
determining a count value of break operating modes in response to receiving the user input indicating the request to enter the break operating mode;
comparing the determined count value of break operating modes to a break operating mode threshold; and
entering the break operating mode in response to the determined count value of break operating modes being less than the break operating mode threshold.

8. The therapy device of claim 7, wherein the stimulation generator comprises a pump, and further comprising a pressure sensor coupled to the pump and configured to measure a pressure output by the pump and to send pressure data to the controller, the pressure data indicative of the pressure output.

9. The therapy device of claim 7, further comprising a temperature sensor, the temperature sensor configured to measure a temperature of the tissue site of the patient and generate temperature data, wherein the controller is further configured to determine an infection, a perfusion level, or both based on the temperature data.

10. The therapy device of claim 7, further comprising a heart rate sensor, the heart rate sensor configured to measure a heart rate of the patient and generate heart rate data, and wherein the controller is further configured to determine an infection, a perfusion level, or both based on the heart rate data.

11. The therapy device of claim 7, further comprising an inertial sensor coupled to the therapy device, the inertial sensor configured to measure an inertia of the therapy device and generate inertia data, wherein the controller is further configured to determine an inertia of the patient based on the inertia data.

12. The therapy device of claim 11, wherein the controller is further configured to select a reduced power mode or an inactive mode based on comparing the inertia of the patient to one or more inertial thresholds.

13. The therapy device of claim 11, wherein the controller further includes a gait analyzer configured to determine a gait based on the inertia data.

14. The therapy device of claim 7, further comprising a moisture sensor coupled to the therapy device, the moisture sensor configured to measure a hydration of tissue of the tissue site, humidity of the tissue site, or both, and generate moisture data, wherein the controller is further configured to determine an infection based on the moisture data.

15. The therapy device of claim 7, further comprising an electrical sensor coupled to the therapy device, the electrical sensor configured to measure an electrical parameter of the stimulation generator and generate electrical data, wherein the electrical parameter includes voltage, current, or both, and wherein the controller is further configured to determine if the therapy device is misplaced, if the therapy device has been removed, or both, based on the electrical data.

16. The therapy device of claim 7, wherein the controller further includes an artificial intelligence (AI) application configured to determine activity, select an operating mode, adjust a threshold, or a combination thereof, based on AI models and sensor data.

17. The therapy device of claim 7, wherein the controller is further configured to output a notification via the therapy device, a notification to a remote device of the patient, a notification to a remote device associated with a care provider, or a combination thereof, responsive to determining that a therapy condition has not been satisfied.

18. A method for providing therapy, the method comprising:
  coupling a therapy device to a user, the therapy device comprising:
    a stimulation generator configured to provide stimulation to a tissue site;
    a sensor;
    a first electrode;
    a second electrode;
    a first section of electrically conductive adhesive electrically coupled with the first electrode;
    a second section of electrically conductive adhesive electrically coupled with the second electrode, the second section of electrically conductive adhesive separate from the first section of electrically conductive adhesive;
  wherein coupling the therapy device to the user is accomplished by coupling the first section of electrically conductive adhesive and the second section of electrically conductive adhesive to the user; and
  identifying a power-on event of the therapy device;
  responsive to the power-on event, operating the stimulation generator of the therapy device in a first operating mode, the first operating mode associated with a first therapy parameter;
  receiving, from the sensor of the therapy device, sensor data indicating activity by the user;
  determining whether the activity satisfies a first activity threshold;
  responsive to determining that the activity satisfies the first activity threshold, operating the stimulation generator in a second operating mode, the second operating mode associated with a second therapy parameter, wherein the first therapy parameter is greater than the second therapy parameter, and wherein the second therapy parameter comprises a voltage, a drive voltage, a current, a duty cycle, a compression pressure, or a combination thereof; and
  operating the stimulation generator in a break operating mode responsive to:
    receiving a user input indicating a request to enter the break operating mode, wherein the break operating mode is a reduced intensity stimulation operating mode or a paused therapy mode;
    determining a count value of break operating modes in response to receiving the user input indicating the request to enter the break operating mode;
    comparing the determined count value of break operating modes to a break operating mode threshold; and
    determining that the determined count value of break operating modes is less than the break operating mode threshold.

19. The method of claim 18, wherein the stimulation generator comprises a pump, and further comprising:
  receiving, from a pressure sensor, pressure data indicating a pressure applied by the pump;
  comparing the pressure to a pressure threshold; and
  responsive to determining that the pressure is greater than the pressure threshold, reducing a duty cycle of the pump.

20. The method of claim 18, further comprising:
  receiving first temperature data from a first temperature sensor coupled to the tissue site;
  receiving second temperature data from a second temperature sensor coupled to a second tissue site;
  determining a temperature difference based on the first temperature data and the second temperature data;
  comparing the temperature difference to a temperature threshold; and
  determining whether the tissue site has an infection based on comparing the temperature difference to the temperature threshold.

* * * * *